US006473637B1

(12) United States Patent
Hayashi

(10) Patent No.: US 6,473,637 B1
(45) Date of Patent: Oct. 29, 2002

(54) METHOD AND APPARATUS FOR DISPLAYING FLUORESCENCE IMAGES

(75) Inventor: Katsumi Hayashi, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 83 days.

(21) Appl. No.: 09/712,918

(22) Filed: Nov. 16, 2000

(30) Foreign Application Priority Data

Nov. 16, 1999 (JP) .......................................... 11-325209

(51) Int. Cl.$^7$ ................................................. A61B 5/00
(52) U.S. Cl. ..................................................... 600/477
(58) Field of Search ............................... 600/160, 109, 600/476, 477, 473, 178, 407

(56) References Cited

U.S. PATENT DOCUMENTS

| 5,590,660 A | 1/1997 | MacAulay et al. ......... 128/664 |
| 6,070,096 A | * 5/2000 | Hayashi ...................... 600/477 |
| 6,293,911 B1 | * 9/2001 | Imaizumi et al. ........... 600/160 |

FOREIGN PATENT DOCUMENTS

JP 10-500588 1/1998 ............ A61B/1/00

* cited by examiner

Primary Examiner—Peter Nerbun
(74) Attorney, Agent, or Firm—Sughrue Mion, PLLC

(57) ABSTRACT

Excitation light and reference light are irradiated to living body tissues, the excitation light causing the living body tissues to produce intrinsic fluorescence. The intrinsic fluorescence, which has been produced from the living body tissues when the excitation light is irradiated to the living body tissues, is detected as an intrinsic fluorescence image signal. Reflected reference light, which has been reflected from the living body tissues when the reference light is irradiated to the living body tissues, is detected as a reference light image signal. Display signals are formed from the intrinsic fluorescence image signal and the reference light image signal. Information concerning the living body tissues is displayed by utilizing the formed display signals. The display signals are formed such that an intensity of the reflected reference light is primarily reflected upon luminance, and a relative intensity of the intrinsic fluorescence is primarily reflected upon color.

20 Claims, 12 Drawing Sheets

F I G. 2
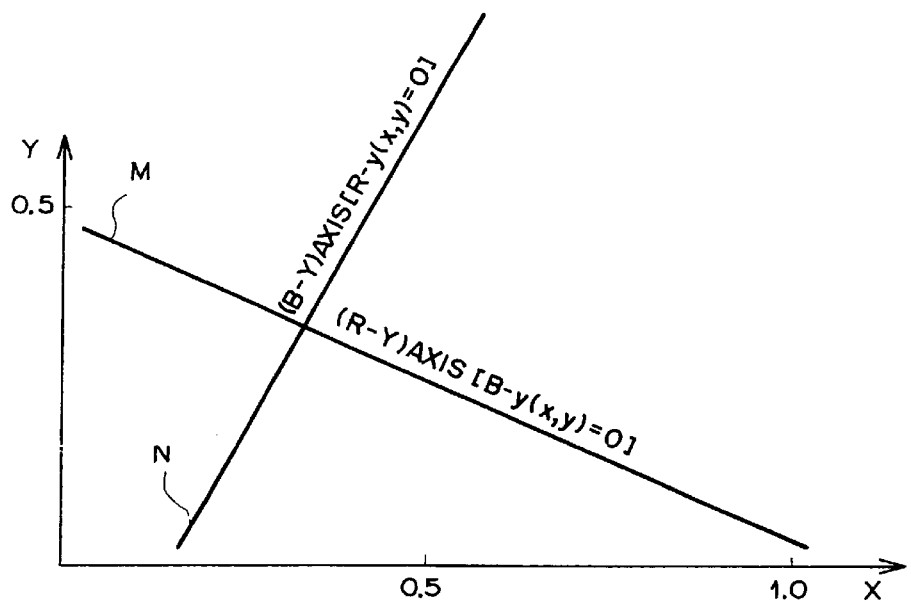
F I G. 3
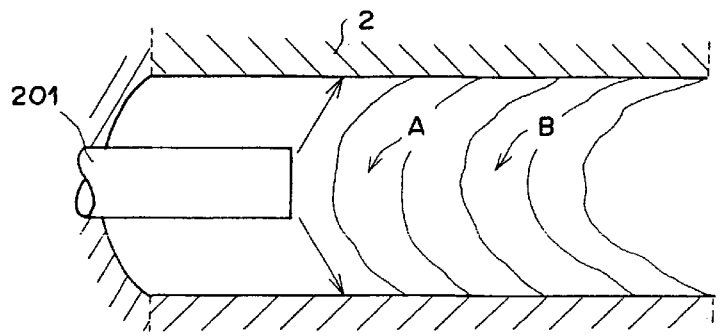
F I G. 4
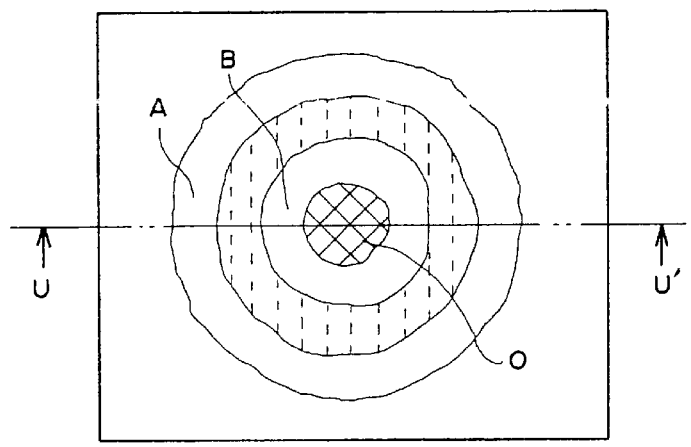

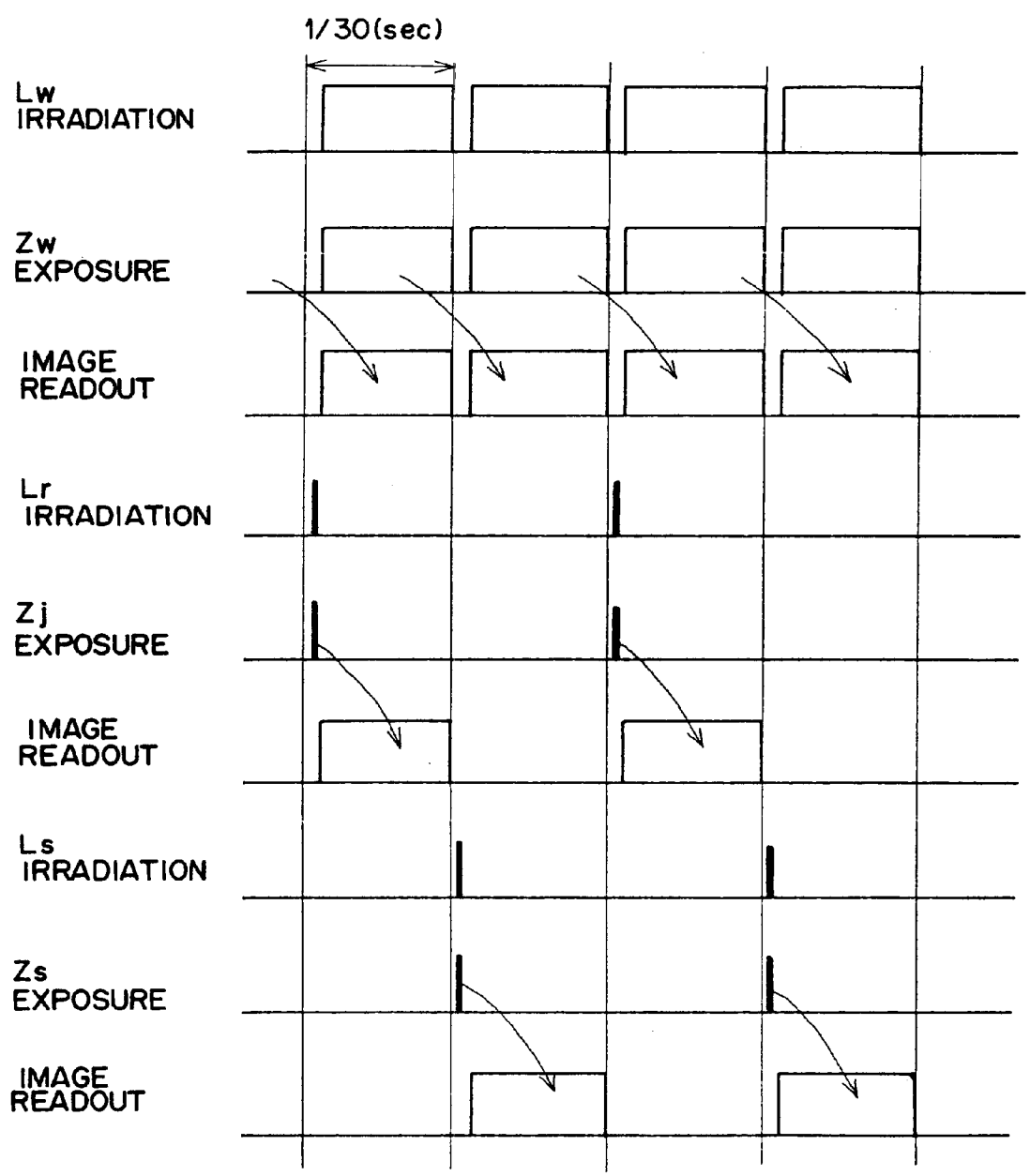

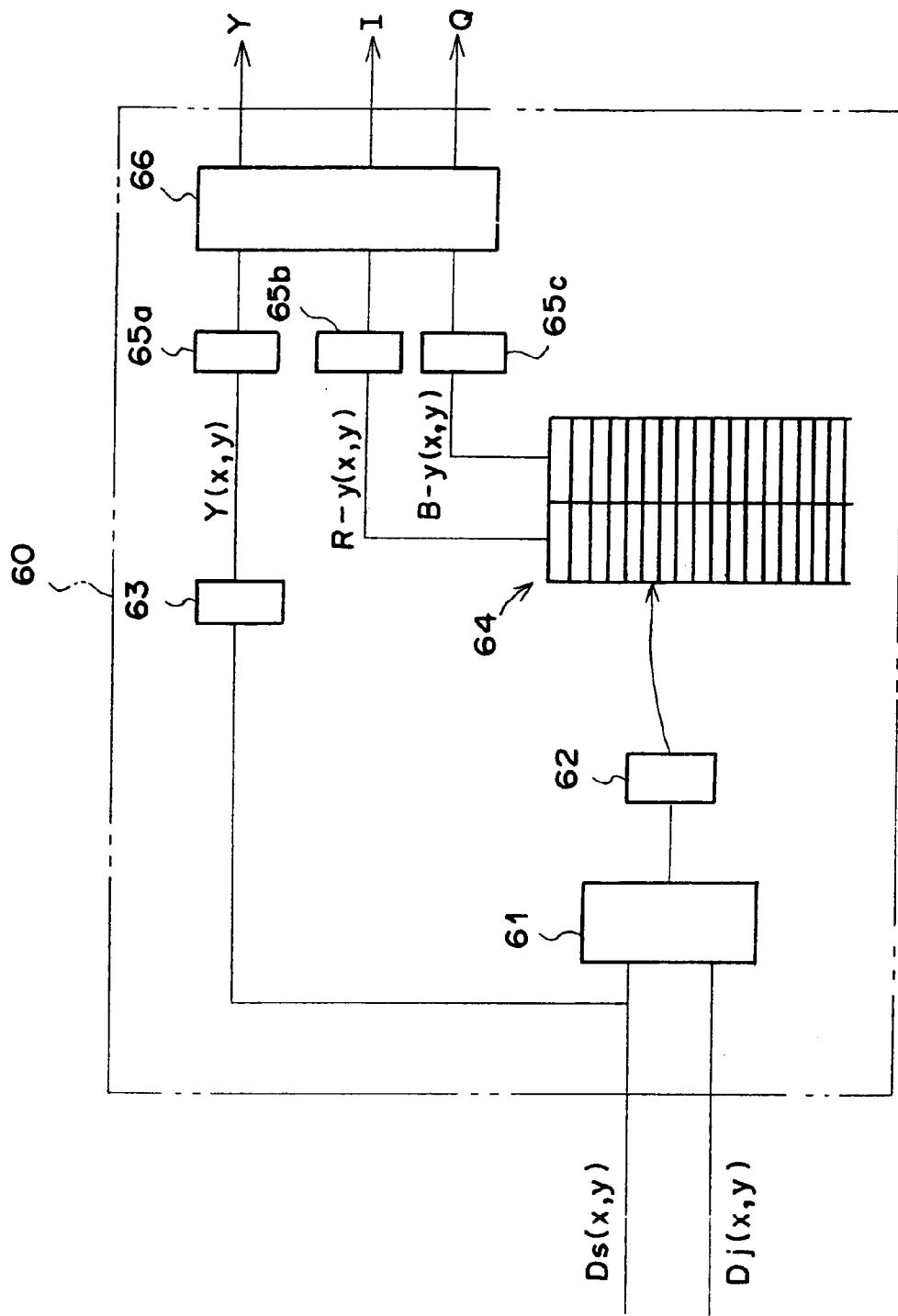

METHOD AND APPARATUS FOR DISPLAYING FLUORESCENCE IMAGES

BACKGROUND OF THE INVENTION

1. Field of the Invention

This invention relates to a method and apparatus for displaying a fluorescence image, wherein intrinsic fluorescence, which is produced from living body tissues when excitation light is irradiated to the living body tissues, is detected and displayed as an image representing information concerning the living body tissues.

2. Description of the Related Art

Research has heretofore been conducted with respect to techniques, wherein intrinsic fluorescence, which is produced by an intrinsic dye in living body tissues when excitation light is: irradiated to the living body tissues, is detected as an image, the image having been formed with the intrinsic fluorescence is analyzed, and a change in tissue condition of the living body tissues due to various kinds of diseases is discriminated in accordance with the results of the analysis.

At the beginning, research was conducted to determine a tissue condition of a living body by paying attention to a variation in intensity of intrinsic fluorescence produced from living body tissues. However, the intensity of the excitation light, which is received by the living body tissues, varies in accordance with a difference in an irradiation angle of the excitation light with respect to the living body tissues, a difference in a distance between an excitation light irradiating system and the living body tissues, and the like. Due to the difference in intensity of the excitation light, which is received by the living body tissues, the intensity of the intrinsic fluorescence produced from the living body tissues varies. Therefore, it has been found that, only with the information representing the intensity of the intrinsic fluorescence, sufficient capability of discriminating the tissue condition of the living body tissues cannot be obtained. Accordingly, there have been proposed, for example, techniques for discriminating a tissue condition of a measuring site by calculating a ratio of an intensity of intrinsic fluorescence, which is produced from a site of living body tissues when the site of the living body tissues is exposed to excitation light, to an intensity of the excitation light, which is received by the site of the living body tissues, i.e. by calculating a value reflecting a fluorescence yield, which value is not affected by the irradiation angle and the irradiation distance of the excitation light.

However, it is not always possible to directly detect the intensity of the excitation light, which is received by each site of the living body tissues. Also, if a distribution of the intensity of the excitation light, which has been reflected from the living body tissues exposed to the excitation light, accurately reflects the distribution of the intensity of the excitation light, which is received by the living body tissues, the distribution of the intensity of the excitation light, which is received by the living body tissues, can be determined by measuring the distribution of the intensity of the excitation light, which has been reflected from the living body tissues. However, of the excitation light irradiated to the living body tissues in order to cause the living body tissues to produce the intrinsic fluorescence, excitation light components having wavelengths on a short wavelength side within the wavelength region of visible light are not subject to uniform absorption by various living body tissues. Therefore, even if the distribution of the intensity of the excitation light, which has been reflected from the living body tissues exposed to the excitation light, is measured, the measured intensity distribution will not accurately reflect the distribution of the intensity of the excitation light, which is received by the living body tissues. Accordingly, as one of techniques for calculating the fluorescence yield, there has been proposed a technique, wherein near infrared light, which is subject to uniform absorption by various living body tissues, is employed as reference light and irradiated to the living body tissues, a distribution of an intensity of reflected reference light, which has been reflected from the living body tissues exposed to the reference light, is detected, and the detected distribution of the intensity of the reflected reference light is utilized in lieu of the distribution of the intensity of the excitation light, which is received by the living body tissues.

Also, a novel technique for discriminating a change in tissue condition of a living body has been proposed in, for example, PCT Japanese Publication No. 10(1998)-500588. With the proposed technique, a two-dimensional image signal, which has been obtained by detecting the intensity of reflected reference light having been reflected from living body tissues, is fed to a red-color channel of a color display device, and an image signal, which has been acquired by detecting the intensity of intrinsic fluorescence having been produced from the living body tissues, is fed to a green-color channel of the color display device. Further, the ratio of the intensity of the intrinsic fluorescence to the intensity of the reflected reference light (i.e., the fluorescence yield) is processed as display signals for altering the color and the luminance, and a change in tissue condition of the living body is displayed as an image.

However, the display luminance of the image formed by feeding the image signal, which has been obtained by detecting the intensity of the reflected reference light having been reflected from the living body tissues, to the red-color channel of the color display device, and feeding the image signal, which has been acquired by detecting the intensity of the intrinsic fluorescence having been produced from the living body tissues, to the green-color channel of the color display device is represented by complicated information comprising a mixture of luminance information, which reflects the shape, the distance, shadows, and the like, of the living body tissues to be seen, and luminance information, which reflects the tissue condition of the living body (i.e., the tissue condition concerning whether the living body tissues are cancerous tissues or normal tissues, and the like). Therefore, when the displayed image is visually seen, it is difficult to make a judgment as to whether a dark area in the image is the one due to a diseased part or the one due to a remote location, a concavity, or the like. As a result, the problems often occur in that the tissue condition of the living body, which is important information for diagnosis, cannot be discriminated correctly. Further, the problems often occur in that, since the intensity of the intrinsic fluorescence produced from a diseased part is low and the display luminance corresponding to the intrinsic fluorescence produced from the diseased part becomes low, a variation in color cannot be discriminated easily, and the presence of the diseased part cannot be found.

Furthermore, ordinarily, a dynamic range of an image displayed on a display device is narrower than the dynamic range of an image formed by a detecting device. Therefore, when the image formed by the detecting device is displayed on the display device, the problems described above are aggravated.

SUMMARY OF THE INVENTION

The primary object of the present invention is to provide a method of displaying a fluorescence image, wherein a tissue condition of a living body and a shape of the living body, which are information concerning living body tissues, are capable of being displayed accurately.

Another object of the present invention is to provide an apparatus for carrying out the method of displaying a fluorescence image.

The present invention provides a first method of displaying a fluorescence image, comprising the steps of:

i) irradiating excitation light and reference light to living body tissues, the excitation light causing the living body tissues to produce intrinsic fluorescence, ii) detecting the intrinsic fluorescence, which has been produced from the living body tissues when the excitation light is irradiated to the living body tissues, and reflected reference light, which has been reflected from the living body tissues when the reference light is irradiated to the living body tissues, respectively as an intrinsic fluorescence image signal and a reference light image signal, iii) forming display signals from the intrinsic fluorescence image signal and the reference light image signal, and iv) displaying information concerning the living body tissues by utilizing the formed display signals, wherein the display signals are formed such that an intensity of the reflected reference light is primarily reflected upon luminance, and a relative intensity of the intrinsic fluorescence is primarily reflected upon color.

In the first method of displaying a fluorescence image in accordance with the present invention, the reflection of the relative intensity of the intrinsic fluorescence upon color may be performed with an additive color mixture process conducted on the intrinsic fluorescence image signal and the reference light image signal.

The present invention also provides a second method of displaying a fluorescence image, comprising the steps of:

i) irradiating excitation light and reference light to living body tissues, the excitation light causing the living body tissues to produce intrinsic fluorescence, ii) detecting the intrinsic fluorescence, which has been produced from the living body tissues when the excitation light is irradiated to the living body tissues, and reflected reference light, which has been reflected from the living body tissues when the reference light is irradiated to the living body tissues, respectively as an intrinsic fluorescence image signal and a reference light image signal, iii) forming display signals from the intrinsic fluorescence image signal and the reference light image signal, and iv) displaying information concerning the living body tissues by utilizing the formed display signals, wherein the display signals are formed such that an intensity of the reflected reference light is primarily reflected upon luminance, and a pattern of a fluorescence spectrum of the intrinsic fluorescence is primarily reflected upon color.

In the second method of displaying a fluorescence image in accordance with the present invention, the reflection of the pattern of the fluorescence spectrum of the intrinsic fluorescence upon color may be performed by utilizing two kinds of intrinsic fluorescence image signal components, which are acquired from two different wavelength regions in the fluorescence spectrum of the intrinsic fluorescence.

The present invention further provides a first apparatus for displaying a fluorescence image, comprising:

i) irradiation means for irradiating excitation light and reference light to living body tissues, the excitation light causing the living body tissues to produce intrinsic fluorescence, ii) detection means for detecting the intrinsic fluorescence, which has been produced from the living body tissues when the excitation light is irradiated to the living body tissues, and reflected reference light, which has been reflected from the living body tissues when the reference light is irradiated to the living body tissues, respectively as an intrinsic fluorescence image signal and a reference light image signal, iii) display signal forming means for forming display signals from the intrinsic fluorescence image signal and the reference light image signal, and iv) displaying means for displaying information concerning the living body tissues by utilizing the formed display signals, wherein the display signal forming means forms the display signals such that an intensity of the reflected reference light is primarily reflected upon luminance, and a relative intensity of the intrinsic fluorescence is primarily reflected upon color.

In the first apparatus for displaying a fluorescence image in accordance with the present invention, the reflection of the relative intensity of the intrinsic fluorescence upon color may be performed with an additive color mixture process conducted on the intrinsic fluorescence image signal and the reference light image signal.

Also, in the first apparatus for displaying a fluorescence image in accordance with the present invention, the relative intensity of the intrinsic fluorescence may be obtained from a division of the intrinsic fluorescence image signal by the reference light image signal.

The present invention still further provides a second apparatus for displaying a fluorescence image, comprising:

i) irradiation means for irradiating excitation light and reference light to living body tissues, the excitation light causing the living body tissues to produce intrinsic fluorescence, ii) detection means for detecting the intrinsic fluorescence, which has been produced from the living body tissues when the excitation light is irradiated to the living body tissues, and reflected reference light, which has been reflected from the living body tissues when the reference light is irradiated to the living body tissues, respectively as an intrinsic fluorescence image signal and a reference light image signal, iii) display signal forming means for forming display signals from the intrinsic fluorescence image signal and the reference light image signal, and iv) displaying means for displaying information concerning the living body tissues by utilizing the formed display signals, wherein the display signal forming means forms the display signals such that an intensity of the reflected reference light is primarily reflected upon luminance, and a pattern of a fluorescence spectrum of the intrinsic fluorescence is primarily reflected upon color.

In the second apparatus for displaying a fluorescence image. in accordance with the present invention, the reflection of the pattern of the fluorescence spectrum of the intrinsic fluorescence upon color may be performed by utilizing two kinds of intrinsic fluorescence image signal components, which are acquired from two different wavelength regions in the fluorescence spectrum of the intrinsic fluorescence.

In the first and second apparatuses for displaying a fluorescence image in accordance with the present invention, the display signal forming means may be provided with a color matrix circuit. In such cases, the color matrix circuit may form R, G, and B signals.

Also, in the first and second apparatuses for displaying a fluorescence image in accordance with the present invention, the irradiation means may be provided with surface sequential irradiation means, and the surface sequential irradiation means may contain the irradiation means for irradiating the reference light.

The term "display signals" as used herein means the signals, from which a visible image is capable of being reproduced by the displaying means. By way of example, the display signals may be constituted of signals according to the NTSC method, signals according to the PAL method, signals according to the SECAM method, RGB signals, and the like.

Also, the term "relative intensity of intrinsic fluorescence" as used herein means the relative intensity of the intrinsic fluorescence, which does not depend upon the position of the living body tissues which position receives the excitation light, and the angle of incidence of the excitation light upon the living body tissues. By way of example, the relative intensity of the intrinsic fluorescence may be represented by the ratio of the intensity of the intrinsic fluorescence, which is produced from the living body tissues when the living body tissues are exposed to the excitation light, to the intensity of the excitation light, which is received by the living body tissues, i.e. may be represented by the fluorescence yield.

Further, the term "reflecting a pattern of a fluorescence spectrum of intrinsic fluorescence upon color" as used herein means both the cases where the pattern by itself of the fluorescence spectrum of the intrinsic fluorescence is reflected upon the color, and the cases where relative intensity representing a value representative of the spectral pattern at a specific wavelength region, or the like, is reflected upon the color. For example, relative intensity representing a value, which is obtained by dividing the intensity of the fluorescence spectrum over the entire wavelength region by the intensity of the fluorescence spectrum at a specific wavelength region, may be reflected upon the color.

With the first method of displaying a fluorescence image and the first apparatus for displaying a fluorescence image in accordance with the present invention, in which the information concerning the living body tissues is displayed by utilizing the display signals, the display signals are formed such that the intensity of the reflected reference light is primarily reflected upon a luminance signal constituting the display signals, and the relative intensity of the intrinsic fluorescence is primarily reflected upon chrominance signals constituting the display signals. In this manner, the intensity of the reflected reference light and the relative intensity of the intrinsic fluorescence are prevented from interfering with each other. Therefore, the tissue condition of the living body tissues and the shape of the living body tissues are capable of being displayed accurately.

With the first method of displaying a fluorescence image and the first apparatus for displaying a fluorescence image in accordance with the present invention, wherein the reflection of the relative intensity of the intrinsic fluorescence upon color is performed with the additive color mixture process conducted on the intrinsic fluorescence image signal and the reference light image signal, the information concerning the living body tissues is capable of being displayed more accurately.

With the first apparatus for displaying a fluorescence image in accordance with the present invention, wherein the relative intensity of the intrinsic fluorescence is obtained from the division of the intrinsic fluorescence image signal by the reference light image signal, the information concerning the living body tissues, which is obtained in accordance with the numerical value, is capable of being displayed more accurately.

With the second method of displaying a fluorescence image and the second apparatus for displaying a fluorescence image in accordance with the present invention, in which the information concerning the living body tissues is displayed by utilizing the display signals, the intensity of the reflected reference light is primarily reflected upon the luminance signal constituting the display signals, and the pattern of the fluorescence spectrum of the intrinsic fluorescence is primarily reflected upon the chrominance signals constituting the display signals. In this manner, the intensity of the reflected reference light and the intensity representing the pattern of the fluorescence spectrum of the intrinsic fluorescence are prevented from interfering with each other. Therefore, the tissue condition of the living body tissues and the shape of the living body tissues are capable of being displayed accurately.

With the second method of displaying a fluorescence image and the second apparatus for displaying a fluorescence image in accordance with the present invention, wherein the reflection of the pattern of the fluorescence spectrum of the intrinsic fluorescence upon color is performed by utilizing two kinds of intrinsic fluorescence image signal components, which are acquired from two different wavelength regions in the fluorescence spectrum of the intrinsic fluorescence, the information concerning the living body tissues is capable of being displayed more accurately.

With the first and second apparatuses for displaying a fluorescence image in accordance with the present invention, wherein the display signal forming means is provided with the color matrix circuit, more accurate display signals are capable of being formed, and the information concerning the living body tissues is capable of being displayed more accurately.

With the first and second apparatuses for displaying a fluorescence image in accordance with the present invention, wherein the display signal forming means is provided with the color matrix circuit, and the color matrix circuit forms the R, G, and B signals, the information concerning the living body tissues is capable of being displayed more accurately.

With the first and second apparatuses for displaying a fluorescence image in accordance with the present invention, wherein the irradiation means is provided with the surface sequential irradiation means, and the surface sequential irradiation means contains the irradiation means for irradiating the reference light, particular irradiation means for irradiating the reference light need not be provided. Therefore, the apparatus for displaying a fluorescence image is capable of being kept simple.

BRIEF DESCRIPTION OF THE DRAWINGS

FIG. 2 is a graph showing positions of color difference signals on a chromaticity coordinate system, FIG. 3 is an explanatory view showing a living body organ containing no diseased tissues, FIG. 4 is an explanatory view showing a distribution of intensity of a reference light image Zs, which is obtained from the living body organ shown in FIG. 3, FIG. 13 is a block diagram showing an internal constitution of a fluorescence image display signal forming device 60.

DESCRIPTION OF THE PREFERRED EMBODIMENTS

The present invention will hereinbelow be described in further detail with reference to the accompanying drawings.

Figure 1:
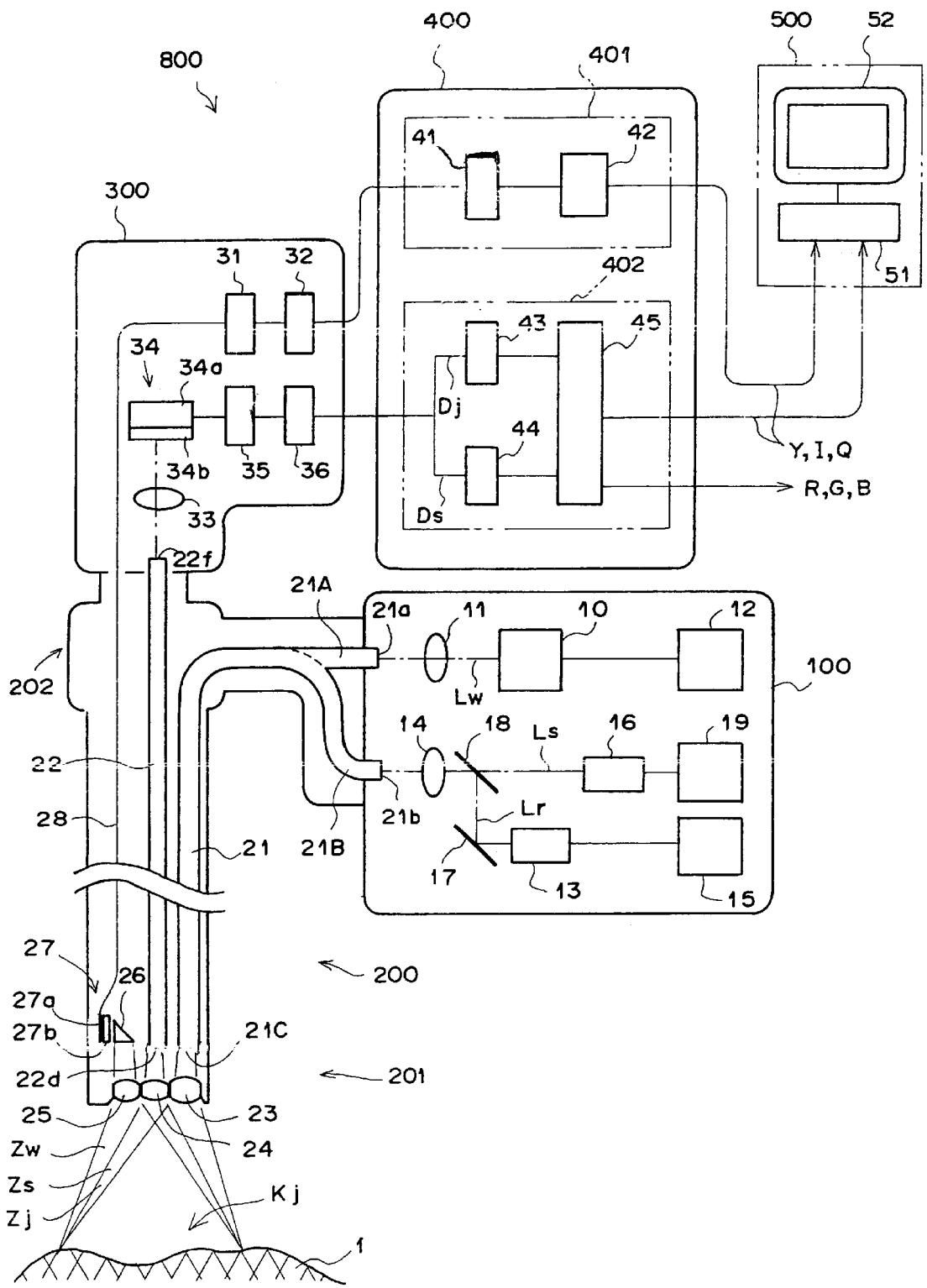
FIG. 1 is a schematic view showing a fluorescence endoscope system, in which a first embodiment of the apparatus for displaying a fluorescence image in accordance with the present invention is employed.

FIG. 1 is a schematic view showing a fluorescence endoscope system, in which a first embodiment of the apparatus for displaying a fluorescence image in accordance with the present invention is employed.

With reference to FIG. 1, a fluorescence endoscope system 800 comprises a light source unit 100 provided with three light sources for respectively producing white light Lw, reference light Ls, and excitation light Lr. The fluorescence endoscope system 800 also comprises an endoscope unit 200 for receiving the excitation light Lr from the light source unit 100, irradiating the excitation light Lr via an illuminating optical fiber 21 to living body tissues 1, and guiding an image, which is formed with intrinsic fluorescence Kj produced from the living body tissues 1 when the living body tissues 1 are exposed to the excitation light Lr, through an image fiber 22. (The image formed with the intrinsic fluorescence Kj will hereinbelow be referred to as the intrinsic fluorescence image Zj.) The fluorescence endoscope system 800 further comprises an imaging unit 300 for detecting the intrinsic fluorescence image Zj, which has been guided through the image fiber 22 of the endoscope unit 200, and forming a two-dimensional digital image signal, which represents the intrinsic fluorescence image Zj. The fluorescence endoscope system 800 still further comprises a display signal processing unit 400 for transforming the two-dimensional image signal, which has been received from the imaging unit 300, into display signals. The fluorescence endoscope system 800 also comprises a displaying unit 500 for receiving the display signals from the display signal processing unit 400 and displaying an image reproduced from the display signals.

The light source unit 100 is connected to an end face 21a of a branch optical fiber 21A, which is branched from the illuminating optical fiber 21, and an end face 21b of a branch optical fiber 21B, which is branched from the illuminating optical fiber 21. The white light Lw, which has been produced by a white light source 10, is converged by a white light converging lens 11 and impinges upon the end face 21a of the branch optical fiber 21A. The excitation light Lr has a wavelength of 410 nm and is produced by an excitation light source 13, which is constituted of an InGaN-LD. The excitation light Lr, which has been produced by the excitation light source 13, is reflected by a reflecting mirror 17, and the direction of the optical path of the excitation light Lr is changed by the reflecting mirror 17 by an angle of approximately 90°. The excitation light Lr is then reflected by a dichroic mirror 18, and the direction of the optical path of the excitation light Lr is changed by the dichroic mirror 18 by an angle of approximately 90°. The dichroic mirror 18 acts so as to reflect light having a wavelength of 410 nm and to transmit light having a wavelength of 780 nm. The excitation light Lr, which has been reflected by the dichroic mirror 18, impinges upon a converging lens 14 and is converged by the converging lens 14. Thereafter, the excitation light Lr impinges upon the end face 21b of the branch optical fiber 21B. The reference light Ls has a wavelength of 780 nm and is produced by a reference light source 16, which is constituted of a GaAs-LD. The reference light Ls, which has been produced by the reference light source 16, passes through the dichroic mirror 18 and is converged by the converging lens 14. The reference light Ls then impinges upon the end face 21b of the branch optical fiber 21B. The white light source 10, the excitation light source 13, and the reference light source 16 are respectively driven by a white light electric power source 12, an excitation light electric power source 15, and a reference light electric power source 19.

The endoscope unit 200 comprises a flexible leading end section 201 and an operating section 202, which is connected to the light source unit 100 and the imaging unit 300. The illuminating optical fiber 21, the image fiber 22, and a cable 28 extend from the leading end section 201 to the operating section 202 in the endoscope unit 200. The illuminating optical fiber 21 guides the excitation light Lr, the reference light Ls, and the white light Lw. The image fiber 22 guides an image, which is formed with the reference light having been reflected by the living body tissues 1 when the reference light Ls is irradiated to the living body tissues 1, and the intrinsic fluorescence image Zj. (The image formed with the reflected reference light will hereinbelow be referred to as the reference light image Zs.) The cable 28 transmits an electric image signal having been formed by a white light imaging device 27, which will be described later.

The white light Lw, which has been produced by the white light source 10, impinges upon the end face 21a of the branch optical fiber 21A, emanates from an end face 21c of the illuminating optical fiber 21, and is irradiated through an illuminating lens 23 to the living body tissues 1. An image, which is formed with the living body tissues 1 when the white light Lw is irradiated to the living body tissues 1, passes through a white light image objective lens 25 and impinges upon a prism 26. (The image, which is formed with the living body tissues 1 when the white light Lw is irradiated to the living body tissues 1, will hereinbelow be referred to as the white light image Zw.) The direction of the optical path of the white light image Zw is changed by the prism 26 by an angle of approximately 90°, and the white light image Zw is formed on the white light imaging device 27. The white light image Zw is converted by the white light imaging device 27 into an electric image signal, and the thus obtained electric image signal is transmitted through the cable 28 into the operating section 202. The white light imaging device 27 comprises an image sensor 27a and a complementary color mosaic filter 27b, which is in close contact with the image sensor 27a. The complementary color mosaic filter 27b comprises yellow (Ye), magenta (Mg), green (G), and cyan (Cy) four-color fine filters, which correspond to each of pixels of the image sensor 27a. Each of the pixels of the image sensor 27a receives light having passed through the-four-color fine filters.

The excitation light Lr, which has been produced by the excitation light source 13, impinges upon the end face 21b of the branch optical fiber 21B, emanates from the end face 21c of the illuminating optical fiber 21, and is irradiated through the illuminating lens 23 to the living body tissues 1. The intrinsic fluorescence image Zj of the intrinsic fluorescence Kj, which is produced from the living body tissues 1 when the living body tissues 1 are exposed to the excitation light Lr, is formed by an objective lens 24 and on an end face 22d of the image fiber 22 and is guided through the image fiber 22 to an end face 22f of the image fiber 22.

The reference light Ls, which has been produced by the reference light source 16, impinges upon the end face 21b of the branch optical fiber 21B, emanates from the end face 21c of the illuminating optical fiber 21, and is irradiated through the illuminating lens 23 to the living body tissues 1. The reference light image Zs of the reference light, which has been reflected from the living body tissues 1 when the reference light Ls is irradiated to the living body tissues 1, is formed by the objective lens 24 and on the end face 22d of the image fiber 22 and is guided through the image fiber 22 to the end face 22f of the image fiber 22.

The imaging unit 300 is connected to the cable 28 and the end face 22f of the image fiber 22. In the imaging unit 300, the image signal representing the white light image Zw, which image signal has been transmitted through the cable 28, is fed into a white light image processing circuit section 31. In the white light image processing circuit section 31, the image signal representing the white light image Zw is subjected to noise suppression processing, defect compensation processing, image signal processing, and the like. (For example, the image signal representing the white light image Zw is subjected to processing performed with a CDS circuit, a contour compensation circuit, a clamp circuit, a gamma compensation circuit, and the like.) Also, in the white light image processing circuit section 31, the image signal representing the white light image Zw is transformed by a color matrix circuit into color difference signals and a luminance signal. The color difference signals and the luminance signal, which have been obtained from the white light image processing circuit section 31, are digitized by a white light image analog-to-digital converter 32 into digital color difference signals and a digital luminance signal.

Also, in the imaging unit 300, the reference light image Zs and the intrinsic fluorescence image Zj, which have been guided through the image fiber 22 to the end face 22f of the image fiber 22, are formed by an image forming lens 33 with different timings on an imaging device 34 and converted by the imaging device 34 into electric image signals. Thereafter, each of the image signal representing the reference light image Zs and the image signal representing the intrinsic fluorescence image Zj is fed into a processing circuit section 35 and subjected to noise suppression processing, defect compensation processing, image signal processing, and the like. Each of the image signals having been obtained from the processing circuit section 35 is then digitized by an analog-to-digital converter 36 into a digital two-dimensional image signal.

The imaging device 34 comprises an image sensor 34a and an excitation light cut-off filter 34b, which is in close contact with the image sensor 34a. The excitation light cut-off filter 34b filters out light having wavelengths of at most 430 nm and transmits only light having wavelengths longer than 430 nm.

The display signal processing unit 400 comprises a white light image signal processing section 401 for performing processing with respect to the signals representing the white light image Zw. The display signal processing unit 400 also comprises a fluorescence image signal processing section 402 for performing processing with respect to the signals representing the intrinsic fluorescence image Zj. The white light image signal processing section 401 comprises a white light image memory 41 for storing the color difference signals and the luminance signal, which have been received from the white light image analog-to-digital converter 32. The white light image signal processing section 401 also comprises a white light image display signal forming device 42 for receiving the color difference signals and the luminance signal from the white light image memory 41, and transforming the color difference signals and the luminance signal into display signals, from which a visible image is capable of being reproduced and displayed by the displaying unit 500. The fluorescence image signal processing section 402 comprises a fluorescence image memory 43 and a reference light image memory 44 for storing the two-dimensional image signals received from the analog-to-digital converter 36. The fluorescence image signal processing section 402 also comprises a fluorescence image display signal forming device 45 for receiving the two-dimensional image signals from the fluorescence image memory 43 and the reference light image memory 44, and transforming the two-dimensional image signals into display signals, from which a visible image is capable of being reproduced and displayed by the displaying unit 500. The fluorescence image display signal forming device 45 is provided with a color matrix circuit, which will be described later.

The displaying unit 500 comprises a superimposer 51 for receiving the display signals from the white light image display signal forming device 42 and the fluorescence image display signal forming device 45 of the display signal processing unit 400, and superimposing the display signals one upon the other to obtain a composed display signal. The displaying unit 500 also comprises a display device 52 for reproducing a visible image from the composed display signal, which has been received from the superimposer 51, and displaying the visible image.

How the fluorescence endoscope system, in which the first embodiment of the apparatus for displaying a fluorescence image in accordance with the present invention is employed, operates will be described hereinbelow. Firstly, how the display signals representing the white light image Zw are formed will be described hereinbelow.

The white light Lw, which has been produced by the white light source 10, is irradiated via the endoscope unit 200 to the living body tissues 1. The white light image Zw, which is formed with the living body tissues 1 when the white light Lw is irradiated to the living body tissues 1, is detected by the white light imaging device 27 via the white light image objective lens 25 and the prism 26. The white light image Zw is converted by the white light imaging device 27 into the electric image signal. The image signal having been obtained from the white light imaging device 27 is transmitted through the cable 28 into the imaging unit 300.

Thereafter, the image signal representing the white light image Zw is processed by the white light image processing circuit section 31 and the white light image analog-to-digital converter 32 of the imaging unit 300 and is stored as the color difference signals and the luminance signal in the white light image memory 41 of the white light image signal processing section 401. Specifically, the intensity information of the light having passed through the yellow (Ye), magenta (Mg), green (G), and cyan (Cy) four-color fine filters of the complementary color mosaic filter 27b of the white light imaging device 27, and having been detected by the white light imaging device 27 is transformed by the color matrix circuit of the white light image processing circuit section 31 into the color difference signals and the luminance signal. The color difference signals and the luminance signal having thus been obtained are then digitized by the white light image analog-to-digital converter 32 into the digital color difference signals and the digital luminance signal. The color difference signals and the luminance signal having been obtained from the white light image analog-to-digital converter 32 are stored in the white light image memory 41. The color difference signals and the luminance signal are then fed from the white light image memory 41 into the white light image display signal forming device 42. The color difference signals and the luminance signal are transformed by the white light image display signal forming device 42 into Y, I, and Q signals according to the NTSC standards, from which signals a visible image is capable of being reproduced and displayed by the displaying unit 500. The Y, I, and Q signals are fed into the displaying unit 500.

How the display signals representing the information concerning the living body tissues are formed will be described hereinbelow. The excitation light Lr, which has been produced by the excitation light source 13, is irradiated via the endoscope unit 200 to the living body tissues 1. The intrinsic fluorescence image Zj of the intrinsic fluorescence Kj, which is produced from the living body tissues 1 when the living body tissues 1 are exposed to the excitation light Lr, passes through the objective lens 24, the image fiber 22, and the image forming lens 33 and is converted by the imaging device 34 into the electric image signal. Thereafter, the thus obtained image signal is processed by the processing circuit section 35 and the analog-to-digital converter 36 of the imaging unit 300 and is stored as an intrinsic fluorescence image signal Dj in the fluorescence image memory 43 of the fluorescence image signal processing section 402. The reference lights, which has been produced by the reference light source 16 is irradiated via the endoscope unit 200 to the living body tissues 1. The reference light image Zs of the reference light, which has been reflected from the living body tissues 1 when the reference light Ls is irradiated to the living body tissues 1, passes through the objective lens 24, the image fiber 22, and the image forming lens 33 and is converted by the imaging device 34 into the electric image signal. Thereafter, the thus obtained image signal is processed by the processing circuit section 35 and the analog-to-digital converter 36 of the imaging unit 300 and is stored as a reference light image signal Ds in the reference light image memory 44 of the fluorescence image signal processing section 402.

The intrinsic fluorescence image signal Dj having been stored in the fluorescence image memory 43 and the reference light image signal Ds having been stored in the reference light image memory 44 are then fed into the fluorescence image display signal forming device 45. The intrinsic fluorescence image signal Dj and the reference light image signal Ds are transformed by the fluorescence image display signal forming device 45 into the display signals according to the NTSC method. The display signals according to the NTSC method, which represent a fluorescence image representing the information concerning the living body tissues, are fed from the fluorescence image display signal forming device 45 into the displaying unit 500.

The display signals according to the NTSC method, which have been formed by the white light image display signal forming device 42, and the display signals according to the NTSC method, which have been formed by the fluorescence image display signal forming device 45, are fed into the superimposer 51 of the displaying unit 500 and combined with each other by the superimposer 51 to form a composed display signal, which represents one image plane. A visible image is then reproduced from the composed display signal and displayed on the display device 52.

How the fluorescence image display signal forming device 45 performs the processing will be described hereinbelow. With the processing performed by the fluorescence image display signal forming device 45, the display signals are formed such that the luminance primarily reflects the intensity of the reflected reference light, and the color primarily reflects the relative intensity of the intrinsic fluorescence.

The display signals according to the NTSC method are derived from the three primary color signals, i.e. a red (R) signal, a green (G) signal, and a blue (B) signal and are formed from a luminance signal Y, which primarily represents the luminance, and color difference signals (R−Y) and (B−Y), which primarily represents the color. According to the NTSC method, when the signals are to be transmitted, an I signal and a Q signal are derived from the color difference signals (R−Y) and (B−Y). Also, the luminance signal Y is allocated to a 4 MHz frequency band width, the I signal is allocated to a 1.5 MHz frequency band width, and the Q signal is allocated to a 0.5MHz frequency band width.

Therefore, when the display signals according to the NTSC method are to be formed, the fluorescence image display signal forming device 45 receives the intrinsic fluorescence image signal Dj and the reference light image signal Ds and forms the luminance signal Y, the color difference signal (R–Y), and the color difference signal (B–Y). (The color difference signal (R–Y) will hereinbelow be referred to as the color difference signal R-y, and the color difference signal (B–Y) will hereinbelow be referred to as the color difference signal B-y.) Specifically, a luminance image signal Y(x,y), a color difference image signal R-y(x,y), and a color difference image signal B-y(x,y), which are the two-dimensional image signals necessary for expressing a certain image plane, are calculated by the color matrix circuit of the fluorescence image display signal forming device 45. The calculations are made with Formula (1) shown below.

$$\begin{bmatrix} Y(x, y) \\ R\text{-}y(x, y) \\ B\text{-}y(x, y) \end{bmatrix} = \begin{bmatrix} 0 & a2 \\ b1 & b2 \\ c1 & c2 \end{bmatrix} \begin{bmatrix} Dj(x, y) \\ Ds(x, y) \end{bmatrix} \quad (1)$$

The luminance image signal Y(x,y) becomes the two-dimensional image signal, which reflects only the reference light image signal Ds(x,y) and does not contain the component of the intrinsic fluorescence image signal Dj(x,y). The luminance image signal Y(x,y) is represented by the formula shown below.

$$Y(x,y) = a2 \times Ds(x,y)$$

The color difference image signal R-y(x,y) and the color difference image signal B-y(x,y) are represented by the formulas shown below.

$$R\text{-}y(x,y) = b1 \times Dj(x,y) + b2 \times Ds(x,y)$$

$$B\text{-}y(x,y) = c1 \times Dj(x,y) + c2 \times Ds(x,y)$$

The two color difference signals act as the signals representing the relative ratio between the reference light image signal Ds and the intrinsic fluorescence image signal Dj, i.e. the fluorescence yield reflecting the tissue condition of the living body tissues 1. Therefore, the display signals are formed such that a change in luminance primarily represents the shape of the living body tissues 1, and a change in color primarily represents the tissue condition of the living body tissues 1.

With the NTSC method, the relationship among the RGB signals, the Y, (R–Y), and (B–Y) signals, and the Y, I, and Q signals is defined as described below. Specifically, as illustrated in FIG. 2, in cases where B-y(x,y)=0, the color difference image signal R-y(x,y) corresponds to a change in color in the region represented by a straight line M on a coordinate system provided with chromaticity axes X and Y. Also, in cases where R-y(x,y)=0, the color difference image signal B-y(x,y) corresponds to a change in color in the region represented by a straight line N on the coordinate system provided with the chromaticity axes X and Y. Further, in cases where the color difference image signal R-y(x,y) and the color difference image signal B-y(x,y) are not equal to 0, the color difference signals correspond to changes in color in the regions sandwiched between the straight line M and the straight line N. Therefore, in cases where the values of the coefficients a2, b1, b2, c1, and c2 in Formula (1) are selected appropriately, the ratio of the intrinsic fluorescence image signal Dj to the reference light image signal Ds is capable of being displayed so as to correspond to an arbitrary color. More specifically, the change in color is expressed with the additive color mixture process performed on the reference light image signal Ds(x, y) and the intrinsic fluorescence image signal Dj(x,y).

Figure 5:
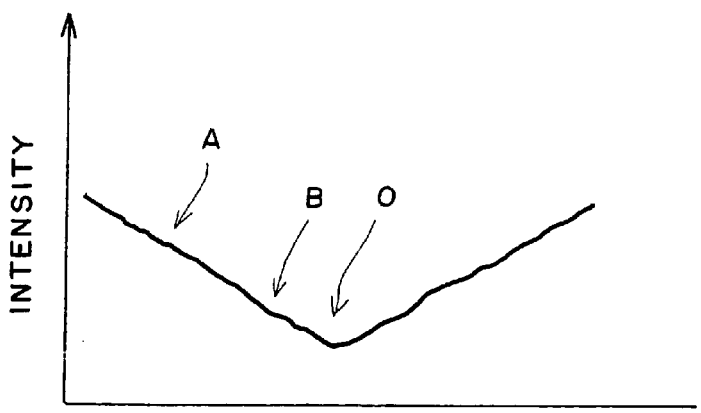
FIG. 5 is a graph showing a distribution of intensity of the reference light image Zs, which distribution is taken along line U—U' of FIG. 4.

By way of example, as illustrated in FIG. 3, in cases where the leading end section 201 of the endoscope unit 200 is inserted into a living body organ 2, which has a tubular shape like the stomach or an intestine and contains no diseased tissues, and measurement of a fluorescence image is performed, the intensity of the reference light Ls, which is received by a site A close to the leading end section 201, is high, and the intensity of the reference light Ls, which is received by a site B remote from the leading end section 201, is low. Therefore, at this time, as illustrated in FIG. 4, the image representing the reference light image Zs detected by the imaging device 34 has an intensity distribution, which is rotationally symmetric around a center region O and in which the intensity becomes low little by little from a peripheral region toward the center region O. Also, as illustrated in FIG. 5, in the intensity distribution of the image representing the reference light image Zs, which distribution is taken along line U—U' of FIG. 4, the intensity becomes low little by little from the peripheral region toward the center region O.

Also, in cases where the excitation light Lr is irradiated to the living body organ 2 in lieu of the reference light Ls, the intensity of the excitation light Lr, which is received by the living body organ 2, has a distribution identical with the distribution of the intensity of the reference light Ls, which is received by the living body organ 2. Therefore, in such cases, the image representing the intrinsic fluorescence image zj detected by the imaging device 34 has an intensity distribution, which is rotationally symmetric around the center region O and in which the intensity becomes low little by little from the peripheral region toward the center region O.

As described above, in cases where diseased tissues are not contained in the living body organ 2, the intensity distribution of the reference light image Zs, which is detected when the reference light Ls is irradiated to the living body organ 2, and the intensity distribution of the intrinsic fluorescence image Zj, which is detected when the excitation light Lr is irradiated to the living body organ 2, takes patterns approximately identical with each other.

Figure 6:
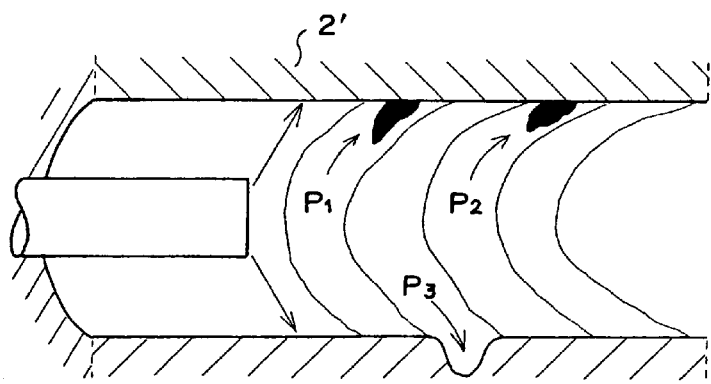
FIG. 6 is an explanatory view showing a living body organ containing diseased tissues.
Figure 7:
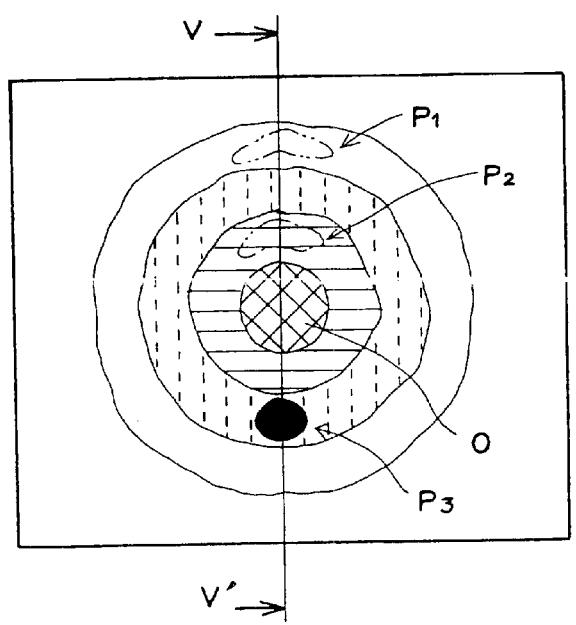
FIG. 7 is an explanatory view showing a distribution of intensity of a reference light image Zs, which is obtained from the living body organ shown in FIG. 6.
Figure 8:
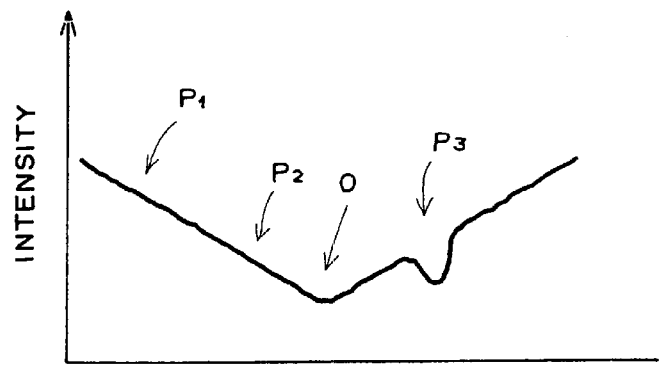
FIG. 8 is a graph showing a distribution of intensity of the reference light image Zs, which distribution is taken along line V—V' of FIG. 7.
Figure 9:
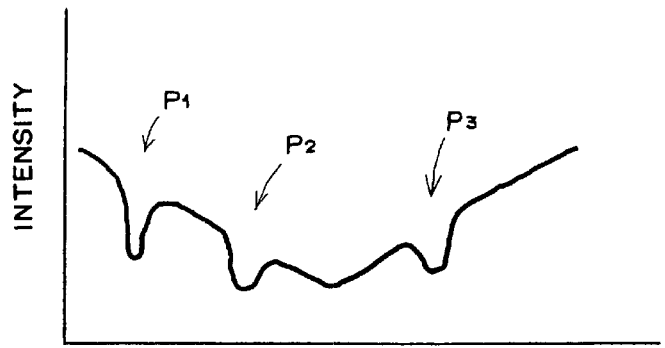
FIG. 9 is a graph showing a distribution of intensity of an intrinsic fluorescence image Zj, which is obtained from the living body organ shown in FIG. 6, the distribution being taken along line V—V' corresponding to line V—V' of FIG. 7.

The reference light Ls has the properties such that the reflection characteristics and the absorption characteristics undergo little variance for the diseased tissues and the normal tissues. Therefore, as illustrated in FIG. 6, in cases where measurement of a fluorescence image is performed with respect to a living body organ 2', in which diseased tissues are present at a site P1 and a site P2 and a concavity is present at a site P3, when the reference light Ls is irradiated from the leading end section 201 of the endoscope unit 200 to the living body organ 2', the intensity distribution representing the reference light image Zs as illustrated in FIG. 7 is obtained. Specifically, in the intensity distribution illustrated in FIG. 7, the intensity does not change at the site P1 and the site P2 and becomes low at the site P3. At the site P3, the intensity of the reference light Ls, which is received by the concavity, becomes low, and therefore the intensity of the reflected reference light coming from the site P3 becomes low. Accordingly, as illustrated in FIG. 8, in the intensity distribution of the image representing the reference light image Zs, which distribution is taken along line V—V' of FIG. 7, the intensity at the site P3 becomes low. In cases where the excitation light Lr is irradiated from the leading end section 201 of the endoscope unit 200 to the living body organ 2', the intrinsic fluorescence is produced from the living body organ 2', such that the intensity of the intrinsic fluorescence produced from the sites P1 and P2 having the diseased tissues is lower than the intensity of the intrinsic fluorescence produced from the other sites having the normal tissues. Therefore, as illustrated in FIG. 9, in the intensity distribution of the image representing the intrinsic fluorescence image Zj, which is obtained from the living body organ 2' shown in FIG. 6, the distribution being taken along line V—V' corresponding to line V—V' of FIG. 7, the intensity becomes low at the sites P1 and P2 and the site P3. At the site P3, the intensity of the excitation light Lr, which is received by the concavity, becomes low, and therefore the intensity of the intrinsic fluorescence produced from the site P3 becomes low. Therefore, the intensities at the sites P1, P2, and P3 in the cross-section taken along line V—V' of the image representing the intrinsic fluorescence image zj become low. Accordingly, as clear from FIG. 8 and FIG. 9, the display signals are formed such that the change In luminance primarily represents the shape, and the change in color primarily represents the tissue condition of the living body tissues.

The intrinsic fluorescence image signal Dj, which has been obtained by detecting the intrinsic fluorescence image Zj, is stored in the fluorescence image memory 43. The reference light image signal Ds, which has been obtained by detecting the reference light image Zs, is stored in the reference light image memory 44.

Thereafter, the intrinsic fluorescence image signal Dj stored in the fluorescence image memory 43 and the reference light image signal Ds stored in the reference light image memory 44 are fed into the fluorescence image display signal forming device 45 and transformed into the Y, I, and Q signals according to the NTSC method.

Figure 10:
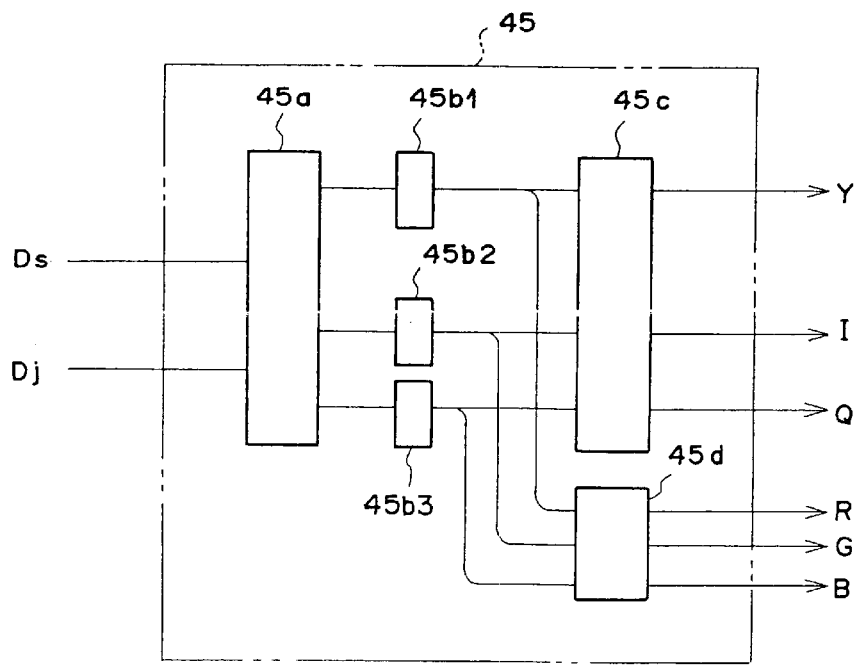
FIG. 10 is a block diagram showing an internal constitution of a fluorescence image display signal forming device 45.

Specifically, as illustrated in FIG. 10, in the fluorescence image display signal forming device 45, the intrinsic fluorescence image signal Dj and the reference light image signal Ds are fed into a color matrix circuit 45a. In the color matrix circuit 45a, the intrinsic fluorescence image signal Dj and the reference light image signal Ds are transformed in accordance with Formula (1) shown above into the luminance image signal Y(x,y), the color difference image signal R-y(x,y), and the color difference image signal B-y(x,y). The luminance image signal Y(x,y), the color difference image signal R-y(x,y), and the color difference image signal B-y(x,y) having thus been obtained are respectively converted by digital-to-analog converters 45b1, 45b2, and 45b3 into analog signals. The thus obtained analog signals are then transformed by an NTSC encoder 45c into the Y, I, and Q signals.

The Y, I, and Q signals according to the NTSC method, which have been obtained from the display signal processing unit 400, are fed into the displaying unit 500 and utilized for reproducing and displaying a visible image.

Figure 11A:
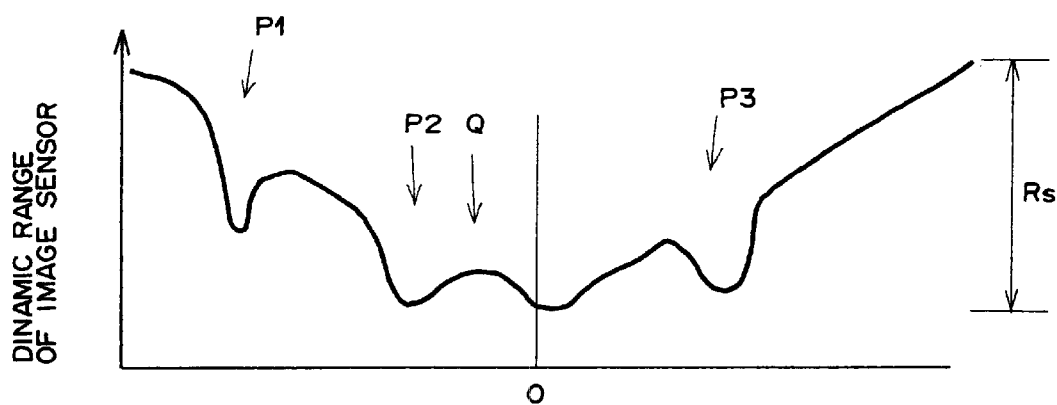
FIG. 11A is a graph showing a dynamic range of an image sensor.
Figure 11B:
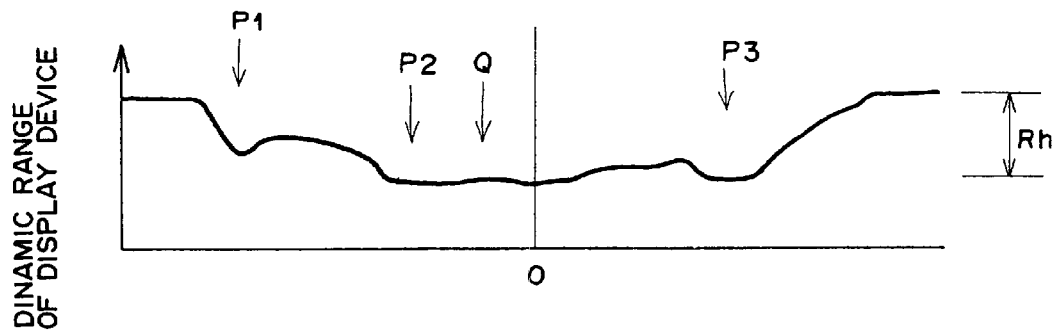
FIG. 11B is a graph showing a dynamic range of a display device, FIG. 12. is a timing chart employed in the fluorescence endoscope system, in which the first embodiment of the apparatus for displaying a fluorescence image in accordance with the present invention is employed.

As described above, with the fluorescence endoscope system, in which the first embodiment of the apparatus for displaying a fluorescence image in accordance with the present invention is employed, the discrimination between the normal tissue concavity, at which the intensity of the received excitation light Lr is low, and the diseased tissues is capable of being made easily as the discrimination of color. (The discrimination was particularly difficult to made in the past.) Also, as illustrated in FIG. 11A and FIG. 11B, a dynamic range Rh of an image displayed on a display device is narrower than a dynamic range Rs of an image formed by an image sensor. Therefore, when the image patterns of sites, which are to be displayed with different luminances, e.g. the image patterns of sites P2 and Q shown in FIG. 11A, are displayed, the problems occur in that the image patterns of the sites are displayed with an identical luminance as illustrated in FIG. 11B, and the presence of the diseased tissues cannot be found. However, with the fluorescence endoscope system employing the first embodiment of the apparatus for displaying a fluorescence image in accordance with the present invention, wherein the discrimination between the normal tissues and the diseased tissues is made as the discrimination of color, the problems can be prevented from occurring in that the presence of the diseased tissues cannot be found. Further, the tissue condition of the living body, which is important information for diagnosis, cannot be displayed correctly.

In the fluorescence endoscope system, in which the first embodiment of the apparatus for displaying a fluorescence image in accordance with the present invention is employed, the irradiation of the white light Lw, the excitation light Lr, and the reference light Ls, the exposures of the image sensors, and the image readouts from the image sensors are performed in accordance with the timing chart shown in FIG. 12. The white light Lw, the excitation light Lr, and the reference light Ls are irradiated with the timings causing no interference and within the period (of $1/15$ second) corresponding to two frames of images, each of which is acquired every $1/30$ second. Therefore, the measurement utilizing each of the white light Lw, the excitation light Lr, and the reference light Ls is not obstructed by the irradiation of the other light. Also, the excitation light Lr is irradiated every $1/15$ second, and the reference light Ls is irradiated every $1/15$ second. The intrinsic fluorescence image zj is thus acquired every $1/15$ second, and the reference light image Zs is acquired every $1/15$ second. Accordingly, the fluorescence image is displayed on the display device 52 as a dynamic image, which is updated every $1/15$ second.

Further, as illustrated in FIG. 10, after the intrinsic fluorescence image signal Dj and the reference light image signal Ds, which have been fed into the color matrix circuit 45a of the fluorescence image display signal forming device 45, have been transformed into the luminance signal Y, the color difference signal (R–Y), and the color difference signal (B–Y), the signals having been obtained from the transformation may be fed into an RGB encoder 45d and transformed into the R, G, and B signals, which are the three primary color signals, in accordance with the formulas shown below, which are defined with the NTSC method.

$Y = +0.59G + 0.30R + 0.11B$ $R-Y = -0.59G + 0.30R - 0.11B$ $B-Y = -0.59G - 0.30R + 0.11B$ $G-Y = +0.59G - 0.30R - 0.11B$

In such cases, it is necessary for a displaying system, which directly receives the R, G, and B signals and is capable of reproducing a visible image from the R, G, and B signals, to be employed as the displaying unit.

As described above, with the fluorescence endoscope system, in which the first embodiment of the apparatus for displaying a fluorescence image in accordance with the present invention is employed, the tissue condition of the living body and the shape of the living body are capable of being displayed accurately.

In the first embodiment described above, the display signals according to the NTSC method are formed.

Alternatively, display signals according to the PAL method, the SECAM method, or the like, may be employed. In such cases, the correspondence relationship may be set with respect to the luminance signal and the color difference signals in the same manner as that described above, and the same effects can thereby be obtained.

A fluorescence endoscope system, in which a second embodiment of the apparatus for displaying a fluorescence image in accordance with the present invention is employed, will be described hereinbelow. The fluorescence endoscope system, in which the second embodiment of the apparatus for displaying a fluorescence image in accordance with the present invention is employed, is constituted in the same manner as that in the fluorescence endoscope system of FIG. 1, in which the first embodiment of the apparatus for displaying a fluorescence image in accordance with the present invention is employed, except that a fluorescence image display signal forming device 60 illustrated in FIG. 13 is employed in lieu of the fluorescence image display signal forming device 45.

With reference to FIG. 13, the fluorescence image display signal forming device 60 comprises a divider 61, a division memory 62, a reference light image memory 63, a look-up table 64, digital-to-analog converters 65a, 65b, 65c, and an NTSC encoder 66. In the divider 61 of the fluorescence image display signal forming device 60, image signal components of the intrinsic fluorescence image signal Dj(x,y) and the reference light image signal Ds(x,y), which image signal components represent corresponding pixels in the intrinsic fluorescence image Zj and the reference light image Zs, are subjected to the division, which is made with the formula shown below.

$$Sub(x,y)=Dj(x,y)/Ds(x,y)$$

The division value Sub(x,y) obtained from the division is stored in the division memory 62. Also, the values R−y(x,y) and B−y(x,y) of the color difference signals, which values correspond to the division value Sub(x,y), are selected from the look-up table 64. The division value Sub(x,y) represents the value, which reflects the fluorescence yield, and the display color is selected appropriately in accordance with the value of the fluorescence yield. The reference light image memory 63 stores the reference light image signal Ds(x,y) and feeds out the information, which represents the value of the reference light image signal Ds(x,y), as the value Y(x,y) of the luminance signal.

The values Y(x,y), R−y(x,y), and B−y(x,y) are respectively converted by the digital-to-analog converter 65a, the digital-to-analog converter 65b, and the digital-to-analog converter 65c into analog signals. The thus obtained analog signals are fed into the NTSC encoder 66. In the NTSC encoder 66, the analog signals are transformed into the Y, I, and Q signals according to the NTSC method. The thus obtained Y, I, and Q signals are fed out from the fluorescence image display signal forming device 60 to the displaying unit 500. The other constitutions and effects are the same as those in the fluorescence endoscope system of FIG. 1, in which the first embodiment of the apparatus for displaying a fluorescence image in accordance with the present invention is employed.

Figure 14:
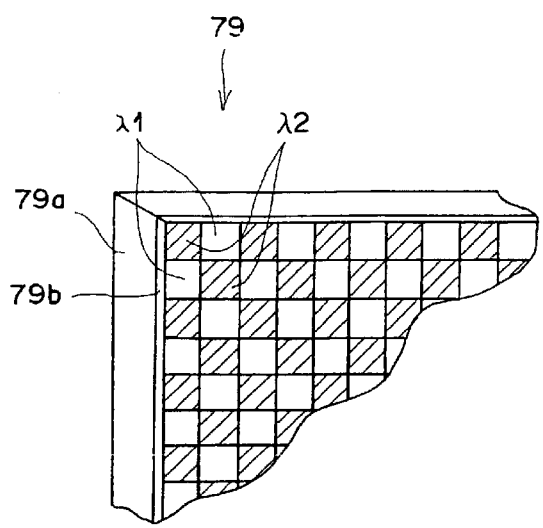
FIG. 14 is a schematic view showing a mosaic filter 79b.
Figure 16:
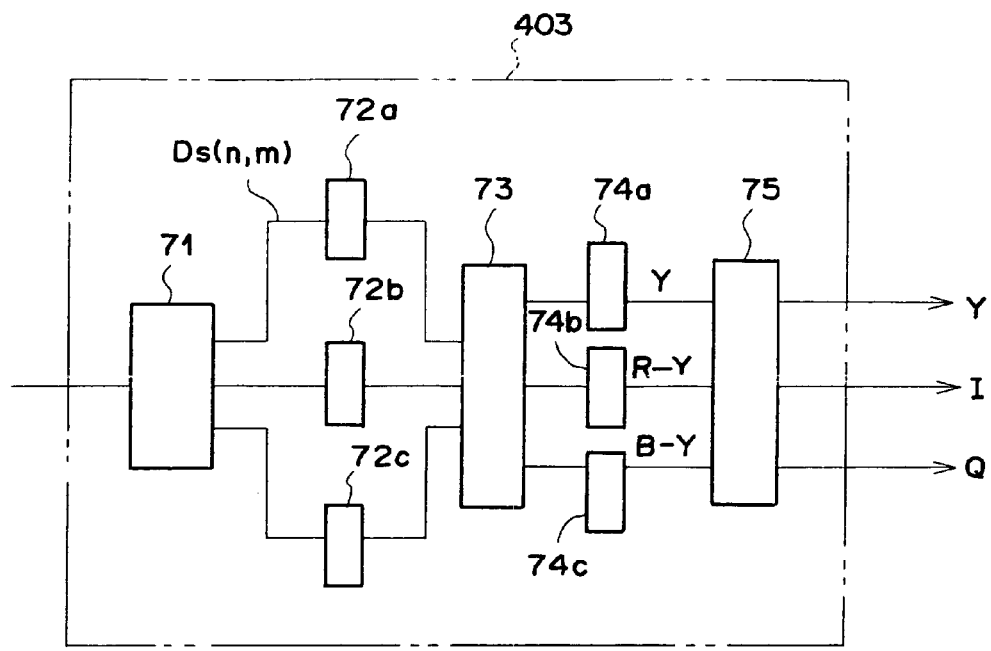
FIG. 16 is a block diagram showing an internal constitution of a fluorescence image signal processing section 403.

A fluorescence endoscope system, in which a third embodiment of the apparatus for displaying a fluorescence image in accordance with the present invention is employed, will be described hereinbelow. The fluorescence endoscope system, in which the third embodiment of the apparatus for displaying a fluorescence image in accordance with the present invention is employed, is constituted in the same manner as that in the fluorescence endoscope system of FIG. 1, in which the first embodiment of the apparatus for displaying a fluorescence image in accordance with the present invention is employed, except that an imaging device 79 illustrated in FIG. 14 is employed in lieu of the imaging device 34, and a fluorescence image signal processing section 403 illustrated in FIG. 16 is employed in lieu of the fluorescence image signal processing section 402. As illustrated in FIG. 14, the imaging device 79 comprises a CCD image sensor 79a and an on-chip filter 79b, which is in close contact with the CCD image sensor 79a.

Figure 15A:
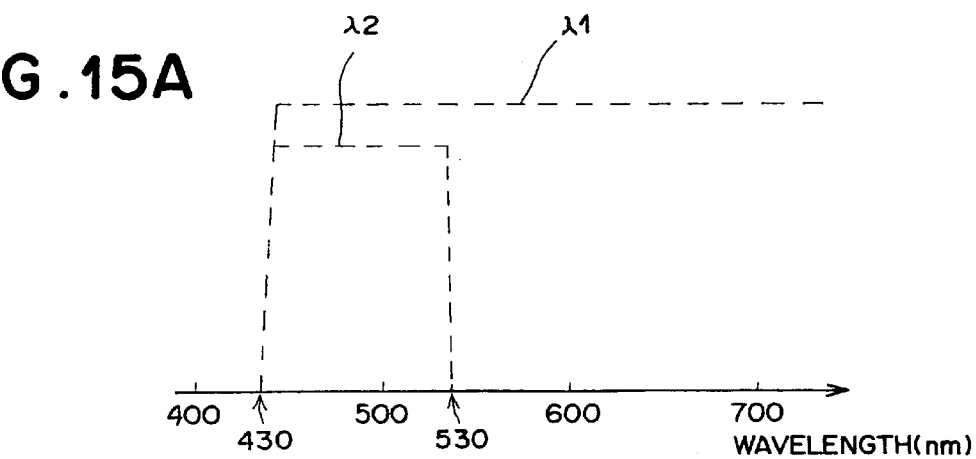
FIG. 15A is a graph showing examples of transmission wavelength regions of fine filters $\lambda 1, \lambda 1, \ldots$ and fine filters $\lambda 2, \lambda 2, \ldots$.

The on-chip filter 79b comprises fine filters $\lambda 2, \lambda 2, \ldots$ and fine filters $\lambda 1, \lambda 1, \ldots$, which are arrayed regularly. As illustrated in FIG. 15A, the fine filters $\lambda 2, \lambda 2, \ldots$ transmit only light having wavelengths falling within the wavelength region of 430 nm to 530 nm . The fine filters $\lambda 1, \lambda 1, \ldots$ transmit only light having wavelengths falling within the wavelength region of at least 430 nm.

Figure 17:
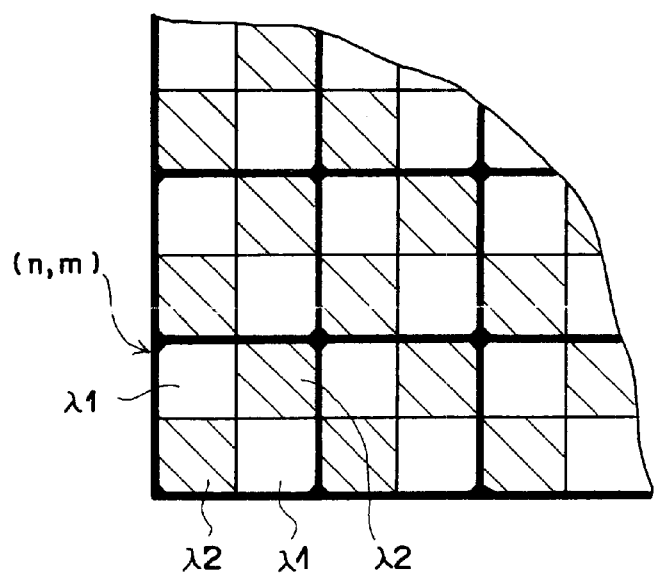
FIG. 17 is an explanatory view showing pixel blocks of fine filters.

The reference light image Zs of the reference light, which has been reflected from the living body tissues 1 when the reference light Ls having a wavelength of 780 nm is irradiated to the living body tissues 1, is formed on the information concerning the imaging device 79. The reference light image Zs does not pass through the regions of the fine filters $\lambda 2, \lambda 2, \ldots$ of the on-chip filter 79b and passes through the regions of the fine filters $\lambda 1, \lambda 1, \ldots$ The reference light image Zs, which has passed through the regions of the fine filters $\lambda 1, \lambda 1, \ldots$, is detected by the CCD image sensor 79a and converted into an electric image signal. The thus obtained image signal is processed by the processing circuit section 35 and the analog-to-digital converter 36. The image signal obtained from the analog-to-digital converter 36 is fed into a pixel block transformer 71 of the fluorescence image signal processing section 403. As illustrated in FIG. 17, in the pixel block transformer 71, with respect to each block (n,m), which contains two fine filters $\lambda 1, \lambda 1$ and two fine filters $\lambda 2, \lambda 2$, the sum of the intensities of the reference light having passed through the two fine filters $\lambda 1, \lambda 1$ is calculated as a value of a reference light image signal Ds(n,m). The reference light image signal Ds(n,m) having been obtained from the pixel block transformer 71 is stored in a reference light image memory 72a.

The intrinsic fluorescence image Zj of the intrinsic fluorescence Kj, which is produced from the living body tissues 1 when the living body tissues 1 are exposed to the excitation light Lr, is formed on the imaging device 79. The intrinsic fluorescence image Zj passes through the regions of the fine filters $\lambda 1, \lambda 1, \ldots$ and the fine filters $\lambda 2, \lambda 2, \ldots$ of the on-chip filter 79b. The intrinsic fluorescence image Zj is then detected by the CCD image sensor 79a and converted into an electric image signal. The thus obtained image signal is processed by the processing circuit section 35 and the analog-to-digital converter 36. The image signal obtained from the analog-to-digital converter 36 is fed into the pixel block transformer 71 of the fluorescence image signal processing section 403. As illustrated in FIG. 17, in the pixel block transformer 71, with respect to each block (n,m), which contains two fine filters $\lambda 1, \lambda 1$ and two fine filters $\lambda 2, \lambda 2$, the sum of the intensities of the intrinsic fluorescence having passed through the two fine filters $\lambda 1, \lambda 1$ is calculated as a value of a first intrinsic fluorescence image signal Dj1(n,m). Also, with respect to each block (n,m), the sum of the intensities of the intrinsic fluorescence having passed through the two fine filters $\lambda 2, \lambda 2$ is calculated as a value of a second intrinsic fluorescence image signal Dj2(n,m).

The first intrinsic fluorescence image signal Dj1(n,m) having been obtained from the pixel block transformer 71 is stored in a fluorescence image memory 72b. The second intrinsic fluorescence image signal Dj2(n,m) having been obtained from the pixel block transformer 71 is stored in a fluorescence image memory 72c.

The reference light image signal Ds(n,m) stored in the reference light image memory 72a, the first intrinsic fluorescence image signal Dj1(n,m) stored in the fluorescence image memory 72b, and the second intrinsic fluorescence image signal Dj2(n,m) stored in the fluorescence image memory 72c are fed into a color matrix circuit 73. In the color matrix circuit 73, calculations are made with Formula (2) shown below.

$$\begin{bmatrix} Y(x,y) \\ R-y(x,y) \\ B-y(x,y) \end{bmatrix} = \begin{bmatrix} 0 & 0 & a3 \\ b1 & b2 & b3 \\ c1 & c2 & c3 \end{bmatrix} \begin{bmatrix} Dj1(x,y) \\ Dj2(x,y) \\ Ds(x,y) \end{bmatrix} \quad (2)$$

specifically, calculations are made with the formulas shown below.

$Y(n,m)=a3 \times Ds(n,m)$ $R-y(n,m)=b1 \times Dj1(n,m)+b2 \times Dj2(n,m)+b3 \times Ds(n,m)$ $B-y(n,m)=c1 \times Dj1(n,m)+c2 \times Dj2(n,m)+c3 \times Ds(n,m)$ In cases where the values of the coefficients b1, b2, b3, c1, c2, and c3 are selected appropriately, a change in color between the normal tissues and the diseased tissues is capable of being set arbitrarily.

The luminance image signal Y(n,m), the color difference image signal R-y(n,m), and the color difference image signal B-y(n,m) having been obtained from the color matrix circuit 73 are then respectively converted by digital-to-analog converters 74a, 74b, and 74c into analog signals. In this manner, a luminance signal Y, a color difference signal (R-Y), and a color difference signal (B-Y) are obtained from the digital-to-analog converters 74a, 74b, and 74c. The luminance signal Y, the color difference signal (R-Y), and the color difference signal (B-Y) are then transformed by an NTSC encoder 75 into Y, I, and Q signals.

In the manner described above, the color matrix circuit 73 makes the calculations on the digital signals. Alternatively, the signals stored in the reference light image memory 72a, the fluorescence image memory 72b, and the fluorescence image memory 72c may be converted by digital-to-analog converters into analog signals, the thus obtained analog signals may be fed into the color matrix circuit, and the calculations may then be performed by the color matrix circuit on the analog signals. In such cases, the digital-to-analog converters 74a, 74b, and 74c shown in FIG. 17 are omitted.

Figure 18:
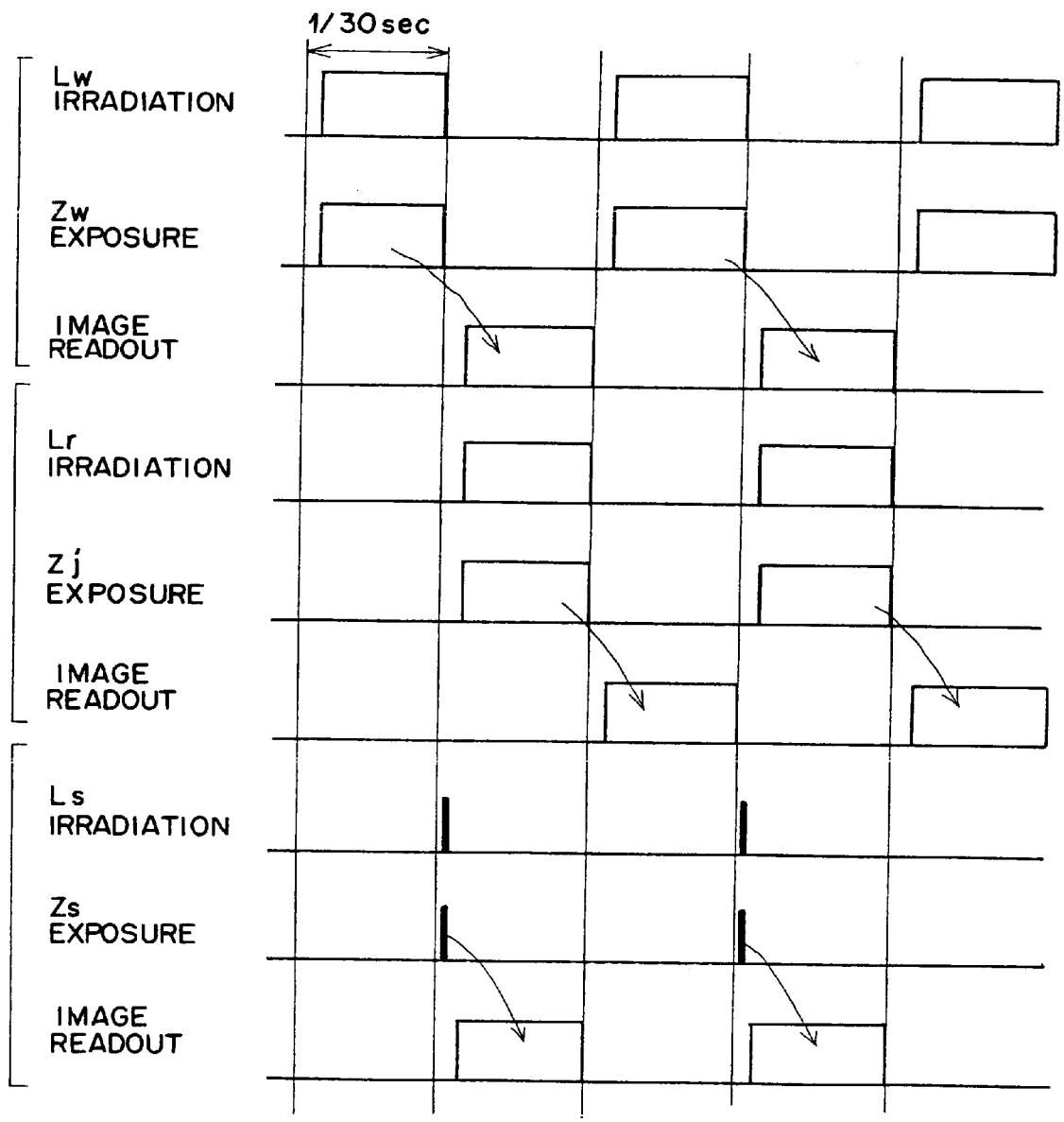
FIG. 18 is a timing chart employed in a fluorescence endoscope system, in which a third embodiment of the apparatus for displaying a fluorescence image in accordance with the present invention is employed.

In the fluorescence endoscope system, in which the third embodiment of the apparatus for displaying a fluorescence image in accordance with the present invention is employed, the irradiation of the white light Lw, the excitation light Lr, and the reference light Ls, the exposures of the image sensors, and the image readouts from the image sensors are performed in accordance with the timing chart shown in FIG. 18. The white light Lw, the excitation light Lr, and the reference light Ls are irradiated with the timings causing no interference and within the period (of $\frac{1}{15}$ second) corresponding to two frames of images, each of which is acquired every $\frac{1}{30}$ second. Therefore, the measurement utilizing each of the white light Lw, the excitation light Lr, and the reference light Ls is not obstructed by the irradiation of the other light. Also, the excitation light Lr is irradiated every $\frac{1}{15}$ second, and the reference light Ls is irradiated every $\frac{1}{15}$ second. The intrinsic fluorescence image Zj is thus acquired every $\frac{1}{15}$ second, and the reference light image Zs is acquired every $\frac{1}{15}$ second. Accordingly, the fluorescence image is displayed on the display device 52 as a dynamic image, which is updated every $\frac{1}{15}$ second.

The reference light image memory 72a, the fluorescence image memory 72b, and the fluorescence image memory 72c act as concurrence adjusting memories for arranging the two-dimensional image signal, which have been acquired in the time series mode, to form concurrent signals. The two-dimensional image signal, which have been acquired with different timings, are read out with predetermined timings and transformed into the luminance signal Y, the color difference signal (R-Y), and the color difference signal (B-Y).

In the manner described above, the tissue condition of the living body and the shape of the living body, which are the information concerning the living body tissues, are capable of being displayed accurately in accordance with the relative intensity of the intrinsic fluorescence and the intensity representing the pattern of the fluorescence spectrum of the intrinsic fluorescence. Specifically, the capability of discrimination between the normal tissues and the diseased tissues is capable of being enhanced markedly in accordance with the characteristics such that the integral intensity of the intrinsic fluorescence varies for the normal tissues and the diseased tissues, and the characteristics such that the integral intensity on the short wavelength side of the normalized spectrum varies for the normal tissues and the diseased tissues.

Figure 15B:
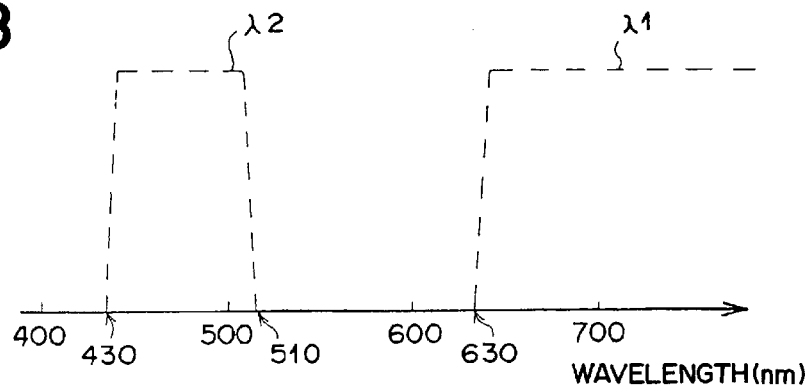
FIG. 15B is a graph showing different examples of the transmission wavelength regions of the fine filters $\lambda 1, \lambda 1, \ldots$ and the fine filters $\lambda 2, \lambda 2, \ldots$.

As illustrated in FIG. 15B, the on-chip filter 79b described above may be replaced by an on-chip filter 79b' comprising fine filters $\lambda 2, \lambda 2, \ldots$, which transmit only light having wavelengths falling within the wavelength region of 430 nm to 510 nm, and fine filters $\lambda 1, \lambda 1, \ldots$, which transmit only light having wavelengths falling within the wavelength region of at least 630 nm. In the on-chip filter 79b', the fine filters $\lambda 1, \lambda 1, \ldots$ and the fine filters $\lambda 2, \lambda 2, \ldots$ are arrayed regularly. Also, the image detection and the processing of the detected image may be performed in the same manner as that described above. In this manner, the two-dimensional image signal obtained with the intrinsic fluorescence having passed through the fine filters $\lambda 1, \lambda 1$, which transmit only light having wavelengths falling within the wavelength region of at least 630 nm, may be employed as the first intrinsic fluorescence image signal Dj1(n,m). Also, the two-dimensional image signal obtained with the intrinsic fluorescence having passed through the fine filters $\lambda 2, \lambda 2$, which transmit only light having wavelengths falling within the wavelength region of 430 nm to 510 nm, may be employed as the second intrinsic fluorescence image signal Dj2(n,m). The first intrinsic fluorescence image signal Dj1(n,m) and the second intrinsic fluorescence image signal Dj2(n,m), which have thus been obtained may be subjected to the calculations made with the formulas described above, i.e. the formulas:

$Y(n,m)=a3 \times Ds(n,m)$ $R-y(n,m)=b1 \times Dj1(n,m)+b2 \times Dj2(n,m)+b3 \times Ds(n,m)$ $B-y(n,m)=c1 \times Dj1(n,m)+c2 \times Dj2(n,m)+c3 \times Ds(n,m)$ The luminance image signal Y(n,m), the color difference image signal R-y(n,m), and the color difference image signal B-y(n,m) may thus be formed from the two-dimensional image signals. The thus formed signals may then be transformed into the Y, I, and Q signals according to the NTSC method. Thereafter, a visible image may be reproduced from the Y, I, and Q signals and displayed.

Specifically, the thus displayed visible image reflects the ratio between the intensity of the intrinsic fluorescence, which has wavelengths falling within the transmission wavelength region of the fine filters λ1, λ1, . . . and the intensity of the intrinsic fluorescence, which has wavelengths falling within the transmission wavelength region of the fine filters λ2, λ2, . . . Therefore, variation of the pattern of the fluorescence spectrum of the intrinsic fluorescence is capable of being discriminated in accordance with a change in display color.

The transmission wavelength region of the fine filters λ2, λ2, . . . should preferably contain the wavelength region in the vicinity of 480 nm, which is associated with the maximum intensity value of the fluorescence spectrum of the intrinsic fluorescence produced from the normal tissues. Also, the transmission wavelength region of the fine filters λ1, λ1, . . . should preferably contain the wavelength region of approximately 630 nm to approximately 700 nm, which wavelength region is associated with the maximum intensity value of the fluorescence spectrum of the intrinsic fluorescence produced from the diseased tissues.

Figure 19:
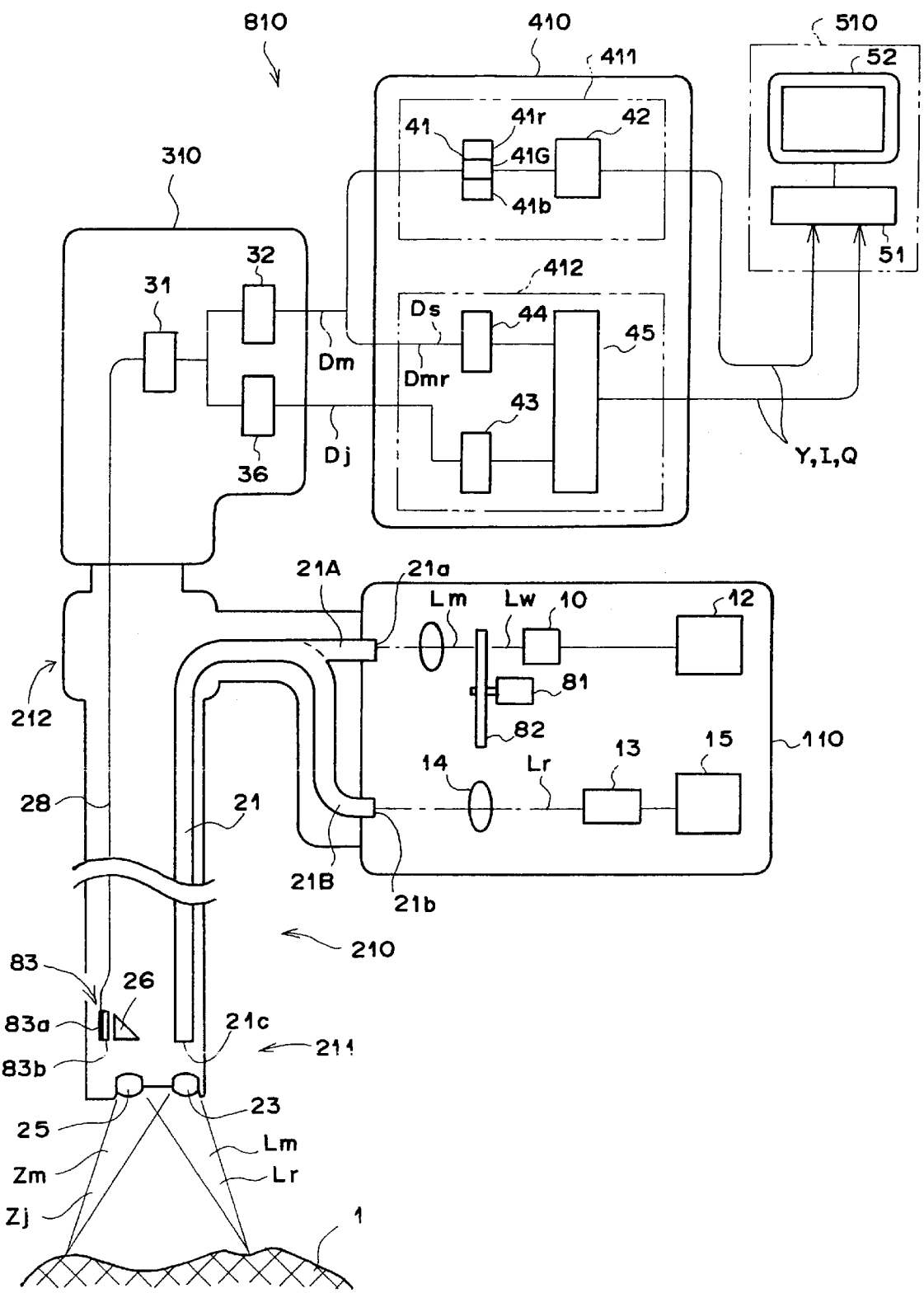
FIG. 19 is a schematic view showing a fluorescence endoscope system, in which a fourth embodiment of the apparatus for displaying a fluorescence image in accordance with the present invention is employed.

A fluorescence endoscope system, in which a fourth embodiment of the apparatus for displaying a fluorescence image in accordance with the present invention is employed, will be described hereinbelow. With reference to FIG. 19, a fluorescence endoscope system 810, in which the fourth embodiment of the apparatus for displaying a fluorescence image in accordance with the present invention is employed, comprises a light source unit 110 provided with two light sources for respectively producing the white light Lw and the excitation light Lr. The fluorescence endoscope system 810 also comprises an endoscope unit 210 for receiving the excitation light Lr from the light source unit 110, irradiating the excitation light Lr via the illuminating optical fiber 21 to the living body tissues 1, detecting the intrinsic fluorescence image Zj, which is formed with the intrinsic fluorescence produced from the living body tissues 1 when the living body tissues 1 are exposed to the excitation light Lr, and converting the intrinsic fluorescence image Zj into an electric image signal. The fluorescence endoscope system 810 further comprises a relay unit 310 for receiving the image signal from the endoscope unit 210, performing noise suppression processing, defect compensation processing, image signal processing, and the like, on the received image signal, and converting the image signal into a digital two-dimensional image signal. The fluorescence endoscope system 810 still further comprises a display signal processing unit 410 for transforming the two-dimensional image signal, which has been received from the relay unit 310, into display signals. The fluorescence endoscope system 810 also comprises a displaying unit 510 for receiving the display signals from the display signal processing unit 410 and displaying an image reproduced from the display signals.

The light source unit 110 is connected to the end face 21a of the branch optical fiber 21A, which is branched from the illuminating optical fiber 21, and the end face 21b of the branch optical fiber 21B, which is branched from the illuminating optical fiber 21. The white light Lw, which has been produced by the white light source 10, is converged by the white light converging lens 11 and impinges upon the end face 21a of the branch optical fiber 21A. A disk-like surface sequential filter 82 is located between the white light source 10 and the white light converging lens 11. The surface sequential filter 82 is provided with R, G, and B filters, i.e. three primary color filters, and secured for rotation to a rotation shaft of a motor 81. When the motor 81 rotates, the white light Lw having been produced by the white light source impinges upon the end face 21a of the branch optical fiber 21A as surface sequential light Lm for RGB surface sequential irradiation.

The excitation light Lr has a wavelength of 410 nm and is produced by the excitation light source 13, which is constituted of the InGaN-LD. The excitation light Lr, which has been produced by the excitation light source 13, is converged by the converging lens 14 and impinges upon the end face 21b of the branch optical fiber 21B. The white light source 10 and the excitation light source 13 are respectively driven by the white light electric power source 12 and the excitation light electric power source 15.

The endoscope unit 210 comprises a flexible leading end section 211 and an operating section 212, which is connected to the light source unit 110 and the relay unit 310. The illuminating optical fiber 21 and the cable 28 extend from the leading end section 211 to the operating section 212 in the endoscope unit 210. The illuminating optical fiber 21 guides the excitation light Lr and the surface sequential light Lm. The cable 28 transmits electric image signals having been formed by detecting images, which are formed with reflected surface sequential light having been reflected by the living body tissues 1 when the surface sequential light Lm is irradiated to the living body tissues 1. (The images formed with the reflected surface sequential light will hereinbelow be referred to as the surface sequential light images Zm.) The cable 28 also transmits the electric image signal having been formed by detecting the intrinsic fluorescence image Zj.

The surface sequential light Lm impinges upon the end face 21a of the branch optical fiber 21A, emanates from the end face 21c of the illuminating optical fiber 21, and is irradiated through the illuminating lens 23 to the living body tissues 1. The surface sequential light images Zm, which are formed with the living body tissues 1 when the RGB surface sequential light Lm is irradiated to the living body tissues 1, pass through the objective lens 25 and impinge upon the prism 26. (The image, which is formed with the living body tissues 1 when the R surface sequential light Lm is irradiated to the living body tissues 1, will hereinbelow be referred to as the R surface sequential light image Zmr. The image, which is formed with the living body tissues 1 when the G surface sequential light Lm is irradiated to the living body tissues 1, will hereinbelow be referred to as the G surface sequential light image Zmg. Also, the image, which is formed with the living body tissues 1 when the B surface sequential light Lm is irradiated to the living body tissues 1, will hereinbelow be referred to as the B surface sequential light image Zmb.) The direction of the optical path of the surface sequential light images Zm is changed by the prism 26 by an angle of approximately 90°, and the surface sequential light images Zm are sequentially formed on an imaging device 83. The surface sequential light images Zm are converted by the imaging device 83 into electric image signals, and the thus obtained electric image signals are transmitted through the cable 28 into the operating section 212. Also, the intrinsic fluorescence image Zj, which is formed with the intrinsic fluorescence produced from the living body tissues 1 when the living body tissues 1 are exposed to the excitation light Lr, is detected by the imaging device 83 and converted into the electric image signal, and the thus obtained electric image signal is transmitted through the cable 28 into the operating section 212.

The imaging device 83 comprises an image sensor 83a and an excitation light cut-off filter 83b, which is in close contact with the image sensor 83a. Therefore, light, from which the excitation light Lr having a wavelength of 410 nm has been filtered out, impinges upon each of pixels of the image sensor 83a.

The relay unit 310 is connected to the cable 28. In the relay unit 310, the image signals representing the surface sequential light images Zm, which image signals have been transmitted through the cable 28, are fed into the processing circuit section 31. In the processing circuit section 31, the image signals representing the surface sequential light images Zm are subjected to noise suppression processing, defect compensation processing, image signal processing, and the like. The image signals representing the surface sequential light images Zm, which image signals have been obtained from the processing circuit section 31, are then digitized by the analog-to-digital converter 32 and are fed out as two-dimensional image signals. Also, the image signal representing the intrinsic fluorescence image Zj is processed by the processing circuit section 31 and the analog-to-digital converter 36 and is fed out as the two-dimensional image signal.

The display signal processing unit 410 comprises a surface sequential light image signal processing section 411 for performing processing with respect to the signals representing the surface sequential light images Zm. The display signal processing unit 410 also comprises a fluorescence image signal processing section 412 for performing processing with respect to the signal representing the intrinsic fluorescence image Zj. The surface sequential light image signal processing section 411 comprises the surface sequential light image memory 41 for storing the two-dimensional image signals, which have been received from the analog-to-digital converter 32. The surface sequential light image signal processing section 411 also comprises the surface sequential light image display signal forming device 42 for receiving the two-dimensional image signals from the surface sequential light image memory 41, and transforming the two-dimensional image signals into display signals, from which a visible image is capable of being reproduced and displayed by the displaying unit 510.

The fluorescence image signal processing section 412 comprises the fluorescence image memory 43 for storing the two-dimensional image signal representing the intrinsic fluorescence image Zj, which image signal is received from the analog-to-digital converter 36. The fluorescence image signal processing section 412 also comprises the reference light image memory 44 for storing the two-dimensional image signal representing the R surface sequential light image Zmr, which image signal is received from the analog-to-digital converter 36. The fluorescence image signal processing section 412 also comprises the fluorescence image display signal forming device 45 for receiving the two-dimensional image signals from the fluorescence image memory 43 and the reference light image memory 44, and transforming the two-dimensional image signals into display signals, from which a visible image is capable of being reproduced and displayed by the displaying unit 510. The fluorescence image display signal forming device 45 is provided with a color matrix circuit. The other constitutions are the same as those in the fluorescence endoscope system of FIG. 1, in which the first embodiment of the apparatus for displaying a fluorescence image in accordance with the present invention is employed.

Figure 20:
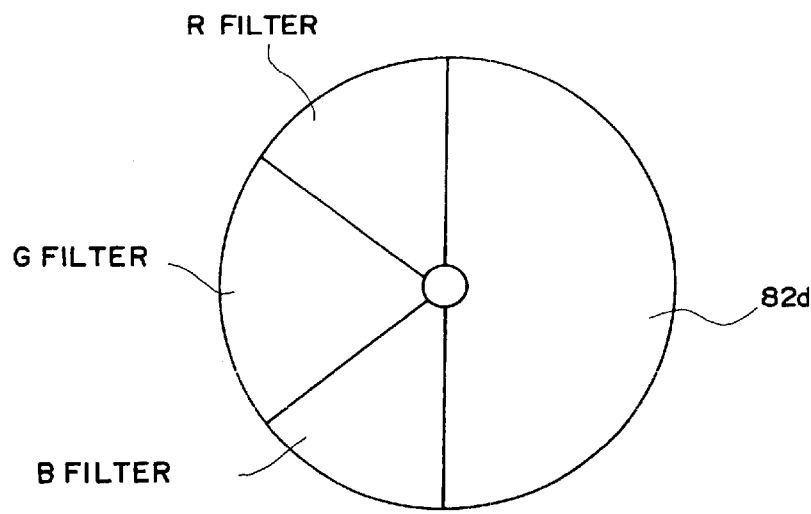
FIG. 20 is an explanatory view showing a surface sequential filter 82.
Figure 21:
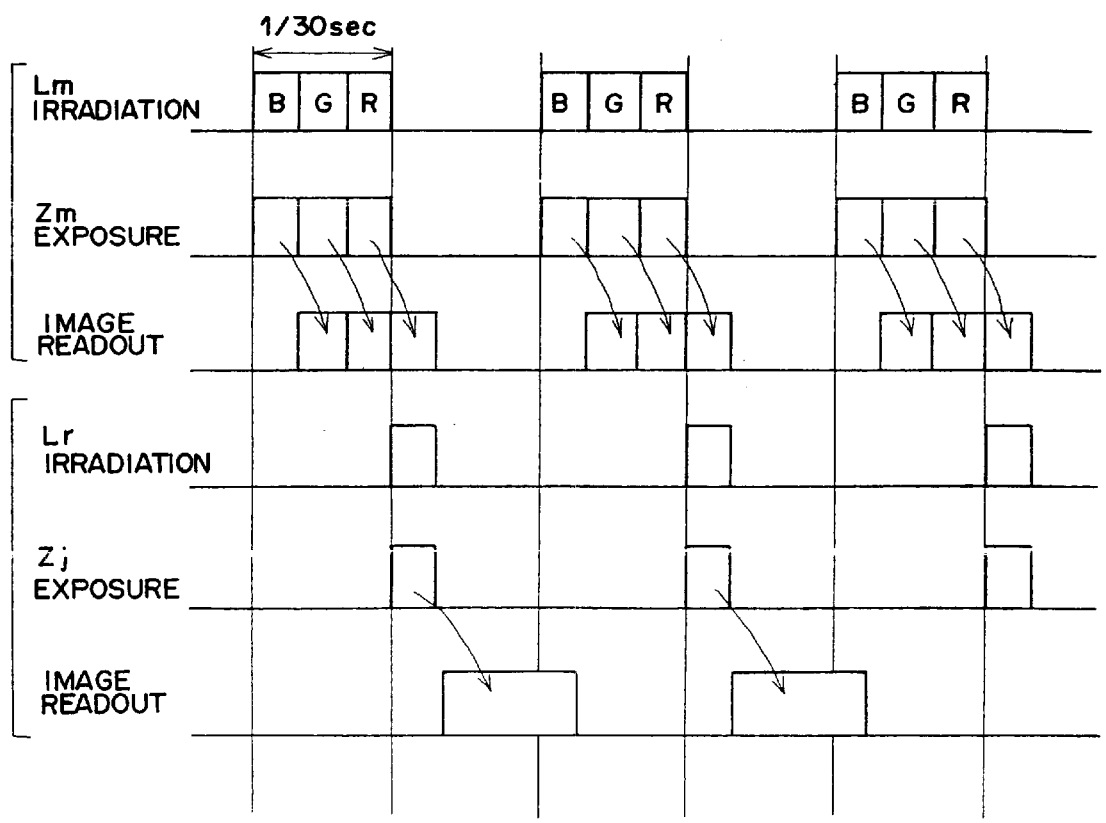
FIG. 21 is a timing chart employed in the fluorescence endoscope system, in which the fourth embodiment of the apparatus for displaying a fluorescence image in accordance with the present invention is employed.

How the fluorescence endoscope system, in which the fourth embodiment of the apparatus for displaying a fluorescence image in accordance with the present invention is employed, operates will be described hereinbelow. As illustrated in FIG. 20, besides the R, G, and B filters, i.e. three primary color filters, the surface sequential filter 82 is provided with a light blocking region 82d. The surface sequential filter 82 is rotated by the motor 81, such that the irradiation of the surface sequential light Lm and the excitation light Lr, the exposures of the image sensor, and the image readouts from the image sensor are performed in accordance with the timing chart shown in FIG. 21. Each of the R surface sequential irradiation, the G surface sequential irradiation, and the B surface sequential irradiation is performed for a period of 1/90 second. Therefore, one series of the RGB surface sequential irradiation is performed for a total period of 1/30 second. Within the period of 1/30 second, the R surface sequential light image Zmr, the G surface sequential light image Zmg, and the B surface sequential light image Zmb, which are formed with the living body tissues 1 when the surface sequential light Lm is irradiated to the living body tissues 1, are detected. For the next period of 1/30 second, the white light Lw having been produced by the white light source 10 is blocked by the light blocking region 82d of the surface sequential filter 82. Also, at this time, the excitation light Lr having been produced by the excitation light source 13 is irradiated to the living body tissues 1, and the intrinsic fluorescence image Zj representing the intrinsic fluorescence produced from the living body tissues 1 is detected.

The image signal representing the intrinsic fluorescence image Zj is processed by the processing circuit a section 31 and digitized by the analog-to-digital converter 36 into a digital two-dimensional image signal. The thus obtained two-dimensional image signal is stored as the intrinsic fluorescence image signal Dj in the fluorescence image memory 43.

The image signals representing the R surface sequential light image Zmr, the G surface sequential light image Zmg, and the B surface sequential light image Zmb are processed by the processing circuit section 31 and digitized by the analog-to-digital converter 32 into digital two-dimensional image signals Dm. The two-dimensional image signals Dm comprise an R image signal Dmr, a G image signal Dmg, and a B image signal Dmb. The R image signal Dmr, the G image signal Dmg, and the B image signal Dmb are respectively stored in an R memory 41r, a G memory 41g, and a B memory 41b of the surface sequential light image memory 41 of the surface sequential light image signal processing section 411. The R image signal Dmr, the G image signal Dmg, and the B image signal Dmb are then transformed by the surface sequential light image display signal forming device 42 into the signals according to the NTSC method, and the thus obtained signals according to the NTSC method are fed into the displaying unit 510. At this time, the R image signal Dmr is also stored as the reference light image signal Ds in the reference light image memory 44 of the fluorescence image signal processing section 412. Specifically, in the first embodiment described above, the image formed with the light having a wavelength of 780 nm falling within the near infrared region, which light has been reflected from the living body tissues 1, is detected, and the image signal representing the thus formed image is employed as the reference light image signal Ds. However, the rate of absorption of light having wavelengths falling within the red wavelength region by the living body tissues 1 is approximately uniform. Therefore, as in the fourth embodiment, the R image signal Dmr obtained with the light having wavelengths falling within the red wavelength region is capable of being utilized as the reference light image signal Ds. Accordingly, with the fourth embodiment, the irradiation of the white light and the irradiation of the reference light are capable of being performed with a common irradiation system, and the detection of the white light image and the detection of the reference light image are capable of being performed with a common imaging device. As a result, the apparatus for displaying a fluorescence image is capable of being kept simple. The other effects are the same as those obtained with the first embodiment described above.

As described above, with the apparatus for displaying a fluorescence image in accordance with the present invention, the tissue condition of the living body and the shape of the living body, which are the information concerning the living body tissues, are capable of being displayed accurately.

In addition, all of the contents of Japanese Patent Application No. 11(1999)-325209 are incorporated into this specification by reference.

What is claimed is:

1. A method of displaying a fluorescence image, comprising the steps of:
   i) irradiating excitation light and reference light to living body tissues, the excitation light causing the living body tissues to produce intrinsic fluorescence,
   ii) detecting the intrinsic fluorescence, which has been produced from the living body tissues when the excitation light is irradiated to the living body tissues, and reflected reference light, which has been reflected from the living body tissues when the reference light is irradiated to the living body tissues, respectively as an intrinsic fluorescence image signal and a reference light image signal,
   iii) forming display signals from the intrinsic fluorescence image signal and the reference light image signal, and
   iv) displaying information concerning the living body tissues by utilizing the formed display signals,
   wherein the display signals are formed such that an intensity of the reflected reference light is primarily indicated as a luminance component signal, and a relative intensity of the intrinsic fluorescence is primarily indicated as a color component signal.

2. A method as defined in Claim 1, wherein the relative intensity of the intrinsic fluorescence indicated as color is performed with an additive color mixture process conducted on the fluorescence image signal and the reference light image signal.

3. A method of displaying a fluorescence image, comprising the steps of:
   i) irradiating excitation light and reference light to living body tissues, the excitation light causing the living body tissues to produce intrinsic fluorescence,
   ii) detecting the intrinsic fluorescence, which has been produced from the living body tissues when the excitation light is irradiated to the living body tissues, and reflected reference light, which has been reflected from the living body tissues when the reference light is irradiated to the living body tissues, respectively as an intrinsic fluorescence image signal and a reference light image signal,
   iii) forming display signals from the intrinsic fluorescence image signal and the reference light image signal, and
   iv) displaying information concerning the living body tissues by utilizing the formed display signals,
      wherein the display signals are formed such that an intensity of the reflected reference light is primarily indicated as a luminance component signal, and a pattern of a fluorescence spectrum of the intrinsic fluorescence is primarily indicated as a color component signal.

4. A method as defined in claim 3, wherein the pattern of the fluorescence spectrum of the intrinsic fluorescence indicated as color is performed by utilizing two kinds of intrinsic fluorescence image signal components, which are acquired from two different wavelength regions in the fluorescence spectrum of the intrinsic fluorescence.

5. An apparatus for displaying a fluorescence image, comprising:
   i) irradiation means for irradiating excitation light and reference light to living body tissues, the excitation light causing the living body tissues to produce intrinsic fluorescence,
   ii) detection means for detecting the intrinsic fluorescence, which has been produced from the living body tissues when the excitation light is irradiated to the living body tissues, and reflected reference light, which has been reflected from the living body tissues when the reference light is irradiated to the living body tissues, respectively as an intrinsic fluorescence image signal and a reference light image signal,
   iii) display signal forming means for forming display signals from the intrinsic fluorescence image signal and the reference light image signal, and
   iv) displaying means for displaying information concerning the living body tissues by utilizing the formed display signals,
      wherein the display signal: forming means forms the display signals such that an intensity of the reflected reference light is primarily indicated as a luminance component signal, and a relative intensity of the intrinsic fluorescence is primarily indicated as a color component signal.

6. An apparatus as defined in claim 5, wherein the relative intensity of the intrinsic fluorescence indicated as color is performed with an additive color mixture process conducted on the intrinsic fluorescence image signal and the reference light image signal.

7. An apparatus as defined in claim 5 wherein the relative intensity of the intrinsic fluorescence is obtained from a division of the intrinsic fluorescence image signal by the reference light image signal.

8. An apparatus as defined in claim 6 wherein the relative intensity of the intrinsic fluorescence is obtained from a division of the intrinsic fluorescence image signal by the reference light image signal.

9. An apparatus for displaying a fluorescence image, comprising:
   i) irradiation means for irradiating excitation light and reference light to living body tissues, the excitation light causing the living body tissues to produce intrinsic fluorescence,
   ii) detection means for detecting the intrinsic fluorescence, which has been produced from the living body tissues when the excitation light is irradiated to the living body tissues, and reflected reference light, which has been reflected from the living body tissues when the reference light is irradiated to the living body tissues, respectively as an intrinsic fluorescence image signal and a reference light image signal,
   iii) display signal forming means for forming 5 display signals from the intrinsic fluorescence image signal and the reference light image signal, and iv) displaying means for displaying information concerning the living body tissues by utilizing the formed display signals, wherein the display signal forming means forms the display signals such that an intensity of the reflected reference light is primarily indicated as a luminance component signal, and a pattern of a fluorescence spectrum of the intrinsic fluorescence is primarily indicated as a color component signal.

10. An apparatus as defined in claim 9, wherein the pattern of the fluorescence spectrum of the intrinsic fluorescence indicated as color is performed by utilizing two kinds of intrinsic fluorescence image signal components, which are acquired from two different wavelength regions in the fluorescence spectrum of the intrinsic fluorescence.

11. An apparatus as defined in claim 5, 6, 7, 8, 9, or 10 wherein the display signal forming means is provided with a color matrix circuit.

12. An apparatus as defined in claim 11 wherein the color matrix circuit forms R, G, and B signals.

13. An apparatus as defined in claim 5, 6, 7, 8, 9, or 10 wherein the irradiation means is provided with surface sequential irradiation means, and the surface sequential irradiation means contains the irradiation means for irradiating the reference light.

14. The method of claim 1, wherein the intrinsic fluorescence is determined without application of a contrast agent to the living body tissues.

15. The method of claim 1, wherein excitation light causing the intrinsic fluorescence has a wavelength within a visible light region of spectra.

16. The method of claim 3, wherein the intrinsic fluorescence is determined without application of a contrast agent to the living body tissues.

17. The method of claim 3, wherein excitation light causing the intrinsic fluorescence has a wavelength within a visible light region of spectra.

18. The apparatus of claim 5, wherein the excitation light causing the intrinsic fluorescence has a wavelength within a visible light region of spectra.

19. The apparatus of claim 9, wherein the excitation light causing the intrinsic fluorescence has a wavelength within a visible light region of spectra.

20. The method of claim 1, wherein the reflected reference light comprises reflected infrared reference light.

* * * * *